(12) United States Patent
Pisano et al.

(10) Patent No.: US 11,819,484 B2
(45) Date of Patent: *Nov. 21, 2023

(54) RETINOID DERIVATIVES WITH ANTITUMOR ACTIVITY

(71) Applicant: BIOGEM S.C. A R.L., Ariano Irpino (IT)

(72) Inventors: Claudio Pisano, Aprilia (IT); Sabrina Dallavalle, Vimercate (IT); Raffaella Cincinelli, Brembate (IT); Lucio Merlini, Viareggio (IT)

(73) Assignee: BIOGEM S.C. A R.L., Ariano Irpino (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/543,479

(22) Filed: Dec. 6, 2021

(65) Prior Publication Data

US 2022/0168252 A1  Jun. 2, 2022

Related U.S. Application Data

(63) Continuation of application No. 17/079,467, filed on Oct. 24, 2020, now Pat. No. 11,364,216, which is a continuation-in-part of application No. 16/337,356, filed as application No. PCT/EP2017/074468 on Sep. 28, 2017, now Pat. No. 10,905,668.

(30) Foreign Application Priority Data

Sep. 29, 2016 (EP) .................................. 16191348

(51) Int. Cl.
| | | |
|---|---|---|
| A61K 31/195 | (2006.01) | |
| A61P 35/00 | (2006.01) | |
| C07C 233/91 | (2006.01) | |
| A61K 9/00 | (2006.01) | |

(52) U.S. Cl.
CPC .......... *A61K 31/195* (2013.01); *A61K 9/0053* (2013.01); *A61P 35/00* (2018.01); *C07C 233/91* (2013.01)

(58) Field of Classification Search
None
See application file for complete search history.

(56) References Cited

U.S. PATENT DOCUMENTS

| | | | | |
|---|---|---|---|---|
| 10,905,668 B2 * | 2/2021 | Pisano | ................ | A61K 33/243 |
| 11,364,216 B2 * | 6/2022 | Pisano | ................ | C07D 309/12 |

* cited by examiner

*Primary Examiner* — Joseph R Kosack
(74) *Attorney, Agent, or Firm* — Greer, Burns & Crain, LTD.; Gregory P. Einhorn

(57) ABSTRACT

The present invention relates to compounds of formula (I) and to pharmaceutical compositions containing them:

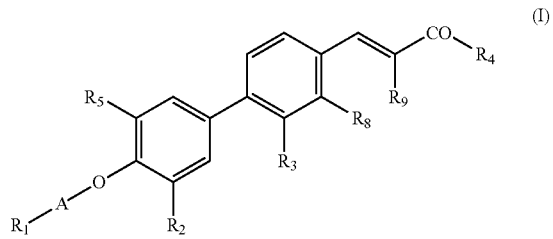

(I)

wherein meanings of the substituents are indicated in the description.

Such compounds for use in the treatment of cancer and other diseases related to altered angiogenesis, such as arthritic pathology, diabetic retinopathy, psoriasis and chronic inflammatory disease, are also within the scope of the present invention.

20 Claims, 3 Drawing Sheets

Table 12

| | ANCI-H460 (NSCLC) | R9A (NSCLC) | A2780 (Ovarian) | A2780-Dx (Ovarian) | MM473 (Meso) | MM487 (Meso) | HT29 (Colon) | SW620 (Colon) | DU145 (Prostate) | B16 (Melanoma) |
|---|---|---|---|---|---|---|---|---|---|---|
| Drug | | | | | $IC_{50} \pm SD$ (μM) | | | | | |
| GEM144 | 0.28 ± 0.01 | 2.2 ± 0.09 | 0.95 ± 0.04 | 0.66 ± 0.008 | 1.4 ± 0.2 | 0.73 ± 0.2 | 1.7 ± 0.1 | 1.4 ± 0.09 | 0.6 ± 0.05 | 0.37 ± 0.03 |
| BIO146 | 1.3 ± 0.05 | 7.3 ± 0.2 | n.e. | n.e. | n.e. | n.e. | n.e. | n.e. | n.e. | n.e. |

FIG. 2

Table 13

| Drug | NB4 (leukemia) | THP-1 (leukemia) | U2932 (lymphoma) | Z138 (lymphoma) |
|---|---|---|---|---|
| | $IC_{50} \pm SD$ (µM) | | | |
| GEM144 | 0.23 ± 0.03 | 0.52 ± 0.02 | 0.77 ± 0.1 | 0.16 ± 0.03 |
| BIO146 | n.e. | n.e. | n.e. | n.e. |

FIG. 3

RETINOID DERIVATIVES WITH ANTITUMOR ACTIVITY

RELATED APPLICATIONS

This application is a continuation of U.S. application Ser. No. 17/079,467, filed Oct. 24, 2020, now pending, which is a continuation-in-part (CIP) of U.S. application Ser. No. 16/337,356, filed Mar. 27, 2019, now U.S. Pat. No. 10,905,668, which is a U.S. national phase patent application claiming benefit of priority under 35 U.S.C. § 371 to Patent Cooperation Treaty (PCT) International patent application number PCT/EP2017/074668, filed Sep. 28, 2017, which claims priority to EP application no. 16191348.8, filed Sep. 29, 2016. The aforementioned applications are expressly incorporated herein by reference in its entirety and for all purposes.

FIELD OF THE INVENTION

The present invention relates to the field of pharmaceutical compounds, in particular retinoid derivatives.

BACKGROUND

Vitamin A and its biologically active derivatives, retinal and retinoic acid, play an important role in vision, are necessary in the reproductive system, act as morphogenic agents during embryonic growth and regulate the growth and differentiation of a vast range of cell types at the basis of the growth of an organism (M. Sporn, A. Roberts, D. Goodman, The Retinoids, Raven Press, New York 1994). The biological action of retinoic acid and its derivatives is mediated by the interaction with nuclear receptors belonging to two families: the first named RAR (retinoic acid receptor) and the second named RXR (retinoid X receptor) (M. A. Asson-Batres, C. Rochette-Egly, The Biochemistry of Retinoic Acid Receptors I: Structure, Activation, and Function at the Molecular Level, Springer, Dordrecht, 2014).

Each family is divided into 3 subtypes ($\alpha$, $\beta$, $\gamma$) coded by three different genes. All-Trans-Retinoic Acid (ATRA) binds to RAR and RXR, whilst 9-cis RA binds only to RXR.

Retinoids, whether natural or synthetic vitamin A analogues, exert a great influence over cellular proliferation, differentiation and apoptosis: these properties are amply exploited in the control of tumoral and dermatological pathologies (B. C. Das et al. Bioorganic & Medicinal Chemistry 22 (2014) 673-683).

It is well known that the growth of a primary tumour is favoured by good vascularization of the tumour tissue. An adequate supply of oxygen and nutrients promotes rapid growth of the tumour itself.

It has been demonstrated that the extent of angiogenesis can be an extremely negative factor in the prognosis of neoplasms (J. A. van der Zee et al., Eur. J. Cancer, 47 (2011) 2576-2584).

It is also known, in the neoplastic field, that a fundamental stage in the biology of the tumour cell is the acquisition of metastasising capability.

The tumour cells that metastasis are able to lose adherence to the surrounding structures, invade blood and lymphatic vessels and colonise other tissues at a distance where they can continue to reproduce themselves.

Metastasising is also a critical event in the clinical history of the disease, being the main cause of death due to cancer. It is closely associated with and facilitated by the presence of vascular tissue in the tumour site or adjacent areas.

The migration of tumour cells across the surrounding structures enables the cells to reach the intratumoral blood vessels, whether pre-existing or formed by neo-angiogenesis, and thus reach the bloodstream (Ray J M., Stetler-Stevenson W G; Eur. Respir. J., 7(11):2062-72, 1994; Stetler-Stevenson W G, Liotta L A, Kleiner D E Jr; FASEB J., 7(15):1434-41, 1993; Sun Y, Ma, L. Trends in Pharmacological Sciences, 36, 349-359, 2015).

Retinoids useful for treating cancer are already known. Acute promielocytic leukemia (APL) can be effectively eradicated by retinoid signaling combined with chemotherapy, and therefore forms the prototype for retinoid-based therapies.

Various cancers other than APL are already being treated with retinoid-based therapies, and several are undergoing clinical evaluation. For several neoplastic diseases, more than one retinoid is being evaluated and many clinical studies are underway to assess their efficacy.

In clinical trials, ATRA and other retinoids alone have shown limited therapeutic success (Connolly R M, Nguyen N K, Sukumar S. Cancer Res 2013; 19:1651-9) that may be attributed, in part, to frequent epigenetic silencing of the retinoic acid receptor (RAR)-$\beta$ (Tang X. H. et al. Annu. Rev. Pathol 2011; 6:345-645). It has been shown that histone deacetylase (HDAC) inhibitors cause re-expression of RAR-$\beta$ and sensitize the cells to treatment (Sirchia S M, et al. Oncogene 2000; 19:1556-63). Therefore combination of retinoids with HDAC inhibitors has been investigated (Pili R, et al. Br. J. Cancer 2012; 106:77-84; Raffoux E. et al. Oncotarget 2010; 1:34-4.) Recently, much interest has been devoted to atypical retinoids or retinoid-related molecules (RRMs), a name that reflects the fact that they exert their anticancer activities independently of the transactivation of the retinoid receptors (RARs, subtypes $\alpha$, $\beta$, and $\gamma$; and RXRs, subtypes $\alpha$, $\beta$, and $\gamma$). RARs and RXRs are members of the nuclear hormone receptor superfamily of ligand-responsive transcription factors, which mediate the multifarious actions of natural and synthetic retinoids in embryo and throughout life.

However, some compounds of this class, containing the adamantyl group, called adamantyl retinoids (Wanka et al. Chem. Rev. 2013, 113, 3516-3604), are known to bind to RARs, such as (6-[(3-adamant-1-yl)-4-hydroxy-phenyl]-2-naphthoic acid, CD437, also called AHPN), which is a RAR$\gamma$ agonist. Other analogs of CD437, such as Adarotene (AHPC), which also binds RAR$\gamma$ and is an apoptogenic agent stronger than CD437, 5-Cl-AHPN and 3-Cl-AHPC, lack RAR transactivation activity while preserving the induction of growth arrest and apoptotic activity in a variety of cancer cell lines (Dawson et al. J. Med. Chem. 2004, 47, 3518). Moreover, 3-Cl-AHPC binds the nuclear hormone receptor small heterodimer partner (SHP) and modulates SHP interaction with the Sin 3A repressor (Farhana et al., Mol. Cancer Ther. 2009, 8, 1625). While still unclear, the mechanism of RRM-mediated cell death, in particular the apoptosis induced by CD437, appears to be largely dependent on cell type. Evidences for caspase-dependent and independent mechanisms via the intrinsic and extrinsic pathways have been provided for these compounds (Lopez-Hernandez et al., Cell Death Differ. 2004, 11, 154-164. Inhibition of IGF-1R and Wnt/$\beta$-Catenin pathways are also involved (L. Farhana et al. J. of Oncology, 2012, 796729).

Atypical retinoid compounds to be used as proapoptotic agents have also been disclosed in Cincinelli et al. Bioorg. Med. Chem. 2007, 15, 4863; Cincinelli R. et al. J. Med. Chem. 2005, 48, 4931-4946; and Zebin et al., Analogues of Orphan Nuclear Receptor Small Heterodimer Partner Ligand and Apoptosis Inducer (E)-4-[3-(1-Adamantyl)-4-hydroxyphenyl]-3-chlorocinnamic Acid. 2. Impact of 3-Chloro Group Replacement on Inhibition of Proliferation and Induction of Apoptosis of Leukemia and Cancer Cell Lines, J. Med. Chem., 2012, 55 (1), pp 233-249.

WO9703682 discloses the use of the above mentioned AHPN compound for treating cancer.

WO9801132, WO2015026990 and WO0156563 disclose adamantyl containing retinoid compounds.

WO2010072727, WO2007000383, WO2003048101 and WO0311808 disclose retinoid derivatives with cytotoxic and/or antitumoral properties. WO2010106135 discloses retinoid derivatives for the treatment of ovarian carcinoma. WO2008077772 discloses a combination comprising an atypical retinoid and a platinum anticancer agent to inhibit tumor growth and tumor migration.

Despite the progress made in recent years, the pharmacological research concerning the discovery of new drugs for the treatment of tumor diseases is still one of the most active fields.

Indeed, there is still a strong need of new compounds capable of blocking or interfering with the tumour diseases.

SUMMARY

It has now been found that new compounds of formula (I), or the pharmaceutically acceptable salts thereof, can be successfully used in the treatment of cancer and other diseases related to altered angiogenesis.

It is an object of the present invention a compound having the following formula (I):

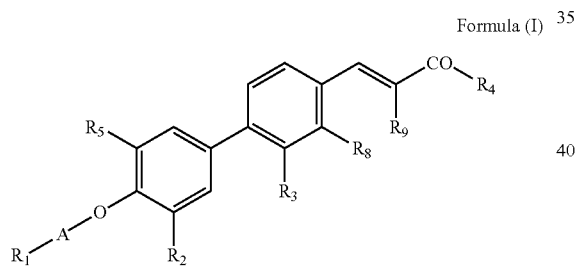

Formula (I)

wherein:
A is selected from the group consisting of: alkylene, alkenylene, alkynylene, COalkylene or is absent,
$R_1$ is selected from the group consisting of: CONHOH, $CH_2OH$, $CH_2SH$, $CH_2SCOCH_3$, $CH_2NHOH$, COOH, COO-alkyl, $COCF_3$, CONHOalkyl, CONHO-oxacycloalkyl, $CONHNH_2$, CONH-aryl, wherein said aryl is optionally substituted with OH and/or $NH_2$, CONHalkyl-S—S-alkyl, CONHalkyl-S—S-alkyl-$NH_2$, CONHalkyl-S—S-alkyl-NHCO—C(=NOH)alkylaryl wherein said aryl is optionally substituted with OH and/or halogen, COalkylCON-Halkyl-S—S-alkyl-NHCO—C(=NOH)alkylaryl wherein said aryl is optionally substituted with OH and/or halogen,
$R_2$ is selected from the group consisting of: H, alkyl, OH, O-alkyl, O-alkenyl, halogen, CN, CHO, COalkyl, COOH, COOalkyl and $CONH_2$,
$R_3$ is selected from the group consisting of: H, alkyl, alkenyl, oxo-alkenyl, hydroxyiminoalkenyl, OH, alkoxy, cycloalkyloxy, arylalcoxy, heterocycloalcoxy, carboxyalcoxy, $CH_2R_6$, $COR_7$, CN, CH=NOH, CH=NOalkylCOOH, CH=NOaryl and CH=NOalkylaryl,
wherein $R_6$ is selected from the group consisting of: OH, alkoxy, $NH_2$, NH-alkyl, N-dialkyl, NHCOOalkyl, NHCOalkyl, aryl, heterocycloalkyl, guanidino optionally substituted with an alkyl or a COOalkyl group, biguanido optionally substituted with an alkyl or an arylalkyl group, and NH—$SO_2$-aryl,
and wherein $R_7$ is selected from the group consisting of: H, OH, O-alkyl, $NH_2$, NHOH, NHaryl, NHalkyl optionally terminally substituted with $NH_2$ or CONHOH,
$R_4$ is selected from the group consisting of: OH, O-alkyl, $NH_2$, NHaryl, NHalkyl, Ndialkyl, NHOH, $NHNH_2$ and $CF_3$, and
$R_5$ is selected from the group consisting of: H, alkyl, cycloalkyl, azacycloalkyl, oxacycloalkyl, aryl, heteroaryl, alkylamminomethyl, arylalkylaminomethyl, heteroarylalkylaminomethyl, wherein each of said groups can be optionally substituted with one or more substituents selected from the group consisting of OH, alkyl, Oalkyl, halogen, $NO_2$, $NH_2$, NHalkyl, Ndialkyl, pyrrolidine, piperidine and morpholine,
provided that when $R_5$ is H $R_1$ is CONHOH,
$R_8$ and $R_9$ are H or together with the carbon atoms to which they are bound form a fused five- or six-membered aromatic or heteroaromatic ring,
wherein alkyl is a $C_1$-$C_{20}$ linear or branched alkyl group, alkenyl is a $C_2$-$C_{20}$ linear or branched alkyl group,
cycloalkyl is a saturated or partially unsaturated $C_3$-$C_{10}$ carbocyclic group comprising one or more condensed rings,
aryl is an aromatic group comprising one or more condensed aromatic rings, heterocycloalkyl and heteroaryl are said cycloalkyl or aryl rings containing one or more heteroatoms selected from the group consisting of N, O and S,
said cycloalkyl, heterocycloalkyl, aryl, heteroaryl, aromatic or heteroaromatic ring being optionally substituted on any position of the ring with one or more substituents selected from the group consisting of halogen, alkyl, linear or branched, O-alkyl, linear or branched, amino, cycloalkyl, heterocycloalkyl, carboxyl, $NO_2$, $NH_2$ and OH,
amino is a group NR'R" wherein each of R' and R" can independently be H or alkyl,
the enantiomers, diastereoisomers, and mixtures thereof, or a pharmaceutically acceptable salt, hydrate or solvate thereof.

It has also been found that the combination of compounds of formula (I) with known chemotherapeutic agents can have a synergistic antitumor effect.

Furthermore, compounds of formula (I) are effective in tumoral cells resistant to other known chemotherapeutic drugs such as, for example, adarotene.

A process for the preparation of the compound of formula (I), as will be better defined below, is also an object of the present invention.

A further object of the invention is a pharmaceutical composition containing as active ingredient a compound of formula (I) and at least one pharmaceutically acceptable vehicle and/or excipient. Such composition can also contain one or more further chemotherapeutic drugs.

It is also an object of the invention the compound of formula (I) for use as a medicament.

A further object of the present invention is a compound of formula (I) for use in the treatment of a disease related to altered angiogenesis. In a preferred embodiment, said disease is selected from the group consisting of arthritic pathology, tumour, metastatization, diabetic retinopathy, psoriasis and chronic inflammatory disease.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference in their entireties for all purposes.

DESCRIPTION OF DRAWINGS

The drawings set forth herein are illustrative of exemplary embodiments provided herein and are not meant to limit the scope of the invention as encompassed by the claims.

FIG. 2 illustrates Table 12, where solid cancer cell lines were exposed to GEM144 and BIO146, as discussed in detail in Example 25, below.

FIG. 3 illustrates Table 13: Human hematological tumor cell lines exposed to GEM144 and BIO146, as discussed in detail in Example 25, below.

Like reference symbols in the various drawings indicate like elements.

DETAILED DESCRIPTION

Definitions

Figure 1:
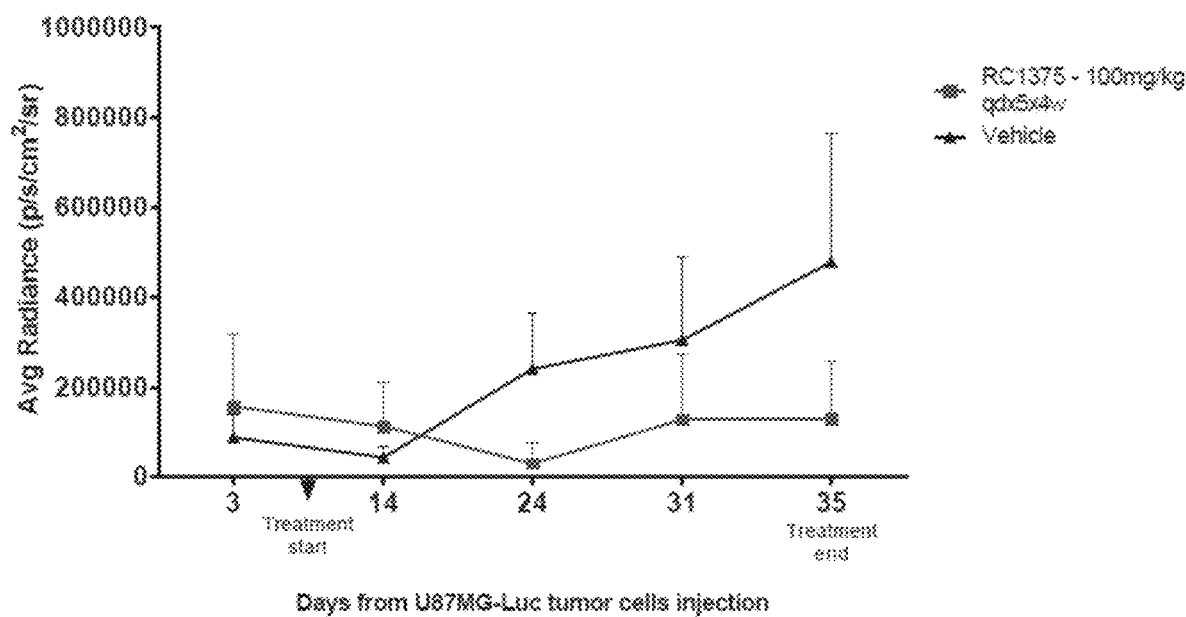
FIG. 1 graphically illustrate an efficacy study of compound 2 (RC1375) in a human glioblastoma orthotopic model; Mice (n=5) were administered intraperitoneally with the compound or vehicle only.

The term "alkyl" refers to linear or branched alkyl groups having from 1 to 20 carbon atoms, preferably having 1 to 12 carbon atoms.

The term "alkylene" refers to a divalent alkyl group having two points of attachment within the compound of the invention. Preferably, it comprises 1 to 20 carbon atoms.

The term "cycloalkyl" refers to a saturated or partially unsaturated carbocyclic group of 3 to 10 carbon atoms. An aromatic group is not intended. The cycloalkyl group can comprise a single ring or multiple condensed rings. Examples of "$C_3$-$C_{10}$-cycloalkyl" include cyclopropyl, cyclobutyl, cyclopentyl, cyclohexyl, norbornyl, adamantyl and the like.

The term "azacycloalkyl" refers to compounds where one or more nitrogen atoms substitute for carbons in the "cycloalkyl" group.

The term "oxacycloalkyl" refers to compounds where one or more oxygen atoms substitute for carbons in the "cycloalkyl" group. A preferred oxacycloalkyl is tetrahydropyran.

The terms "heterocycloalkyl" and "heterocycle" refer to a saturated or partially unsaturated (but not aromatic) cycloalkyl ring, preferably a five-, six- or seven-membered ring, containing one or more nitrogen, oxygen or sulfur atoms; the rings may be substituted with one or more groups selected for example from alkyl, hydroxyl and carboxyl. Preferred heterocycloalkyl include pyrrolidine, piperidine, piperazine, morpholine and tetrahydropyran.

The term "aryl" refers to aromatic rings, for example phenyl, naphthyl, anthracenyl, optionally substituted with halogen, alkyl, linear or branched, O-alkyl, linear or branched, amino, cycloalkyl, heterocycloalkyl, carboxyl, $NO_2$, $NH_2$ and/or OH.

The term "heteroaryl" refers to heteroaromatic rings, for example furan, thiophene, pyridine, pyrimidine, quinoline, quinazoline, optionally substituted with halogen, alkyl, linear or branched, O-alkyl, linear or branched, amino, cycloalkyl, heterocycloalkyl, carboxyl, $NO_2$, $NH_2$ and/or OH.

The term "amino" refers to a group NRR' wherein each of R and R' can independently be H or alkyl.

The term "aminocarbonylalkyl" refers to an alkyl group substituted by an aminocarbonyl moiety.

The term "aminocarbonyl" refers to a group of formula —NR'R"CO— wherein each of R' and R" can independently be H or alkyl.

An alkyl group can be for example methyl, ethyl, n-propyl, i-propyl, n-butyl, t-butyl. It can be linear or branched.

An alkylene group is preferably methylene, ethylene, trimethylene, propylene, tetramethylene or dimethylethylene.

The halogen is selected from the group consisting of: fluorine (F), chlorine (Cl), bromine (Br) and iodine (I).

Any nitrogen group can be protected. The protective group is preferably selected from tert-butoxycarbonyl, benzyloxycarbonyl and 9-fluorenylmethyloxycarbonyl.

In a preferred embodiment of the present invention, the compound of formula (I) has a cycloalkyl as $R_5$, more preferably it has an adamantyl group as $R_5$.

In another preferred embodiment, $R_4$ is OH or O-alkyl.

In a preferred embodiment, $R_1$ is CONHOH.

In preferred embodiments, $R_2$ is H.

In preferred embodiments, $R_3$ is H.

In even more preferred embodiments, both $R_2$ and $R_3$ are H.

In a more preferred embodiment, A is alkylene, preferably $C_1$-$C_4$alkylene, more preferably methylene, and $R_1$ is CONHOH. Even more preferably, in this embodiment $R_4$ is OH and $R_5$ is adamantyl.

Preferably, $R_3$ is selected from the group consisting of: H, alkyl, alkenyl, oxo-alkenyl, hydroxyiminoalkenyl, OH, alkoxy, $CH_2R_6$, $COR_7$, CN, CH=NOH, CH=NOalkylCOOH, CH=NOaryl and CH=NOalkylaryl.

Preferably, $R_4$ is selected from the group consisting of: OH, O-alkyl, $NH_2$, NHOH, $NHNH_2$ and $CF_3$.

The pharmaceutical acceptable salts of the compound of formula (I) are included in the scope of the invention.

Pharmaceutical acceptable salts are salts which retain the biological activity of the base and are derived from such known pharmacologically acceptable acids such as, e.g., hydrochloric, hydrobromic, sulfuric, phosphoric, nitric, fumaric, succinic, oxalic, malic, tartaric, maleic, citric, methanesulfonic or benzoic acid and others commonly used in the art. A preferred salt is a salt of the trifluoroacetic acid.

Also, pharmaceutically acceptable hydrates or solvates of the compound of formula (I) are included in the scope of the present invention. In particular, they can be any hydrate or solvate commonly used in the art.

Preferred compounds according to the present invention are:
3-[3'-Adamantan-1-yl-4'-(3-hydroxycarbamoyl-propoxy)-biphenyl-4-yl]-acrylic acid (1) (RC 1315)
3-[3'-Adamantan-1-yl-4'-(4-hydroxycarbamoyl-butoxy)-biphenyl-4-yl]-acrylic acid (2) (RC 1375)
3-[3'-Adamantan-1-yl-4'-(7-hydroxycarbamoyl-heptyloxy)-biphenyl-4-yl]-acrylic acid (3) (RC 1268)

2-(2-{4-[3-Adamantan-1-yl-4'-(2-carboxy-vinyl)-biphenyl-4-yloxy]-butyrylamino}-ethyldisulfanyl)-ethyl-ammonium; trifluoroacetate (4) (RC 1363)

3-{3'-Adamantan-1-yl-4'-[3-(2-{2-[3-(3-bromo-4-hydroxy-phenyl)-2-hydroxyimino-propionylamino]-ethyldisulfanyl}-ethylcarbamoyl)-propoxy]-biphenyl-4-yl}-acrylic acid (5) (RC 1338)

3-{3'-Adamantan-1-yl-4'-[3-(2-{2-[3-(3-bromo-4-hydroxy-phenyl)-2-hydroxyimino-propionylamino]-ethyldisulfanyl}-ethylcarbamoyl)-propionyloxy]-biphenyl-4-yl}-acrylic acid (6) (AB 514)

3-[3'-Adamantan-1-yl-4'-(4-carboxy-butoxy)-biphenyl-4-yl]-acrylic acid (7) (RC 1401)

3-(3'-Adamantan-1-yl-4'-hydroxycarbamoylmethoxybiphenyl-4-yl)-acrylic acid (8) (MIR002)

3-{3'-Adamantan-1-yl-4'[(tetrahydropyran-2-yloxycarbamoyl)-methoxy]-biphenyl-4-yl}-acrylic acid (9) (BIO 49)

3-(3'-Adamantan-1-yl-4'-carboxymethoxy-biphenyl-4-yl)-acrylic acid (10) (GEM 66)

3-{3'-Adamantan-1-yl-4'-[2-(tetrahydro-pyran-2-yloxycarbamoyl)-ethoxy]-biphenyl-4-yl}-acrylic acid (11) (GEM 57)

3-[3'-Adamantan-1-yl-4'-(2-hydroxycarbamoyl-ethoxy)-biphenyl-4-yl]-acrylic acid (12) (GEM 60)

6-{3-Adamantan-1-yl-4-[(tetrahydro-pyran-2-yloxycarbamoyl)-methoxy]-phenyl}-naphthalene-2-carboxylic acid (13) (GEM 59)

6-(3-Adamantan-1-yl-4-hydroxycarbamoylmethoxy-phenyl)-naphthalene-2-carboxylic acid (14) (GEM 61)

3-[3'-Adamantan-1-yl-4'-(hydroxyl-buthoxy)-biphenyl-4-yl]-acrylic acid (15) (BIO4)

3-(3'-Adamantan-1-yl-4'-hydroxyaminomethoxy-biphenyl-4-yl)-acrylic acid trifluoroacetate (16) (GEM 95)

3-(3'-adamantan-1-yl-4'-hydrazinocarbonylmethoxy-biphenyl-4-yl)-acrylic acid trifluoroacetate (17) (GEM 93)

3-(4'-Hydroxycarbamoylmethoxy-biphenyl-4-yl)-acrylic acid (18) (GEM 103)

3-[3'-(1,5-Diaza-bicyclo[3.3.1]non-9-yl)-4'-(4-hydroxycarbamoyl-butoxy)-biphenyl-4-yl]-acrylic acid (19)

3-[4'-(4-Hydroxycarbamoyl-butoxy)-3'-(1,3,5,7-tetraaza-tricyclo[3.3.1.1 3,7]dec-2-yl)-biphenyl-4-yl]-acrylic acid (20)

3-[4'-(4-Hydroxycarbamoyl-butoxy)-3'-(1-methyl-cyclohexyl)-biphenyl-4-yl]-acrylic acid (21)

3-Phenyl-4'-(4-hydroxycarbamoyl-butoxy)-biphenyl-4-yl]-acrylic acid (22)

3-(4'-(4-Hydroxycarbamoyl-butoxy)-3'-f{[(naphthalen-2-ylmethyl)-amino]-methyl}-biphenyl-4-yl)-acrylic acid (23)

3-(4'-(4-Hydroxycarbamoyl-butoxy)-3'-{[(quinolin-7-ylmethyl)-amino]-methyl}-biphenyl-4-yl)-acrylic acid (24)

3-(4'-(4-Hydroxycarbamoyl-butoxy)-3'-f{[(8-hydroxy-5-nitro-quinolin-7-ylmethyl)-amino]-methyl}-biphenyl-4-yl)-acrylic acid (25)

Formulae of the above mentioned compounds are represented in the following table:

| | |
|---|---|
| 1<br>RC1315 | 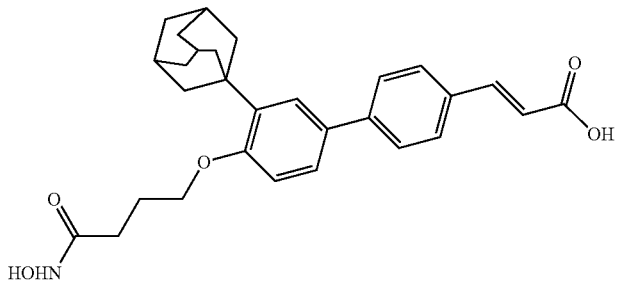 |
| 2<br>RC 1375 | 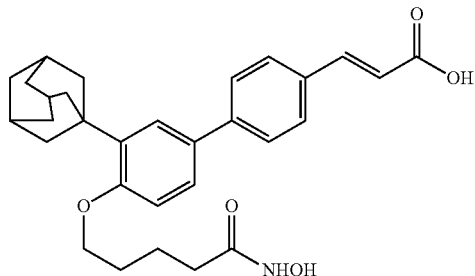 |
| 3<br>RC 1268 | 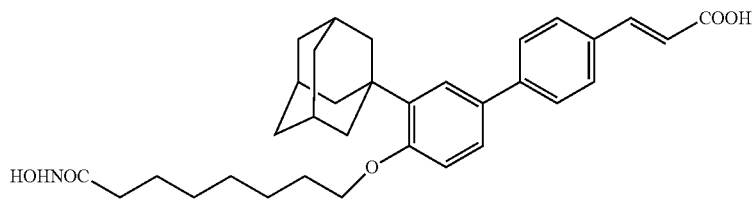 |

-continued
4
RC 1363
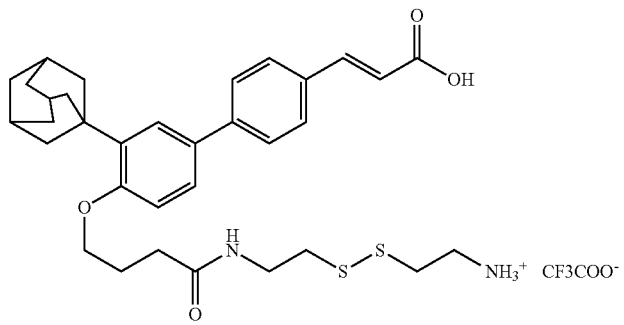 [SMILES: [NH3+]CCSSCCNC(=O)CCCOc1ccc(-c2ccc(/C=C/C(=O)O)cc2)cc1C12CC3CC(CC(C3)C1)C2]
5
RC 1338
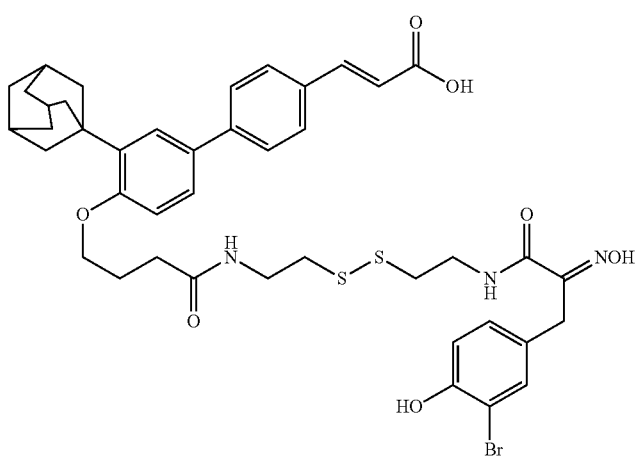
6
AB 514
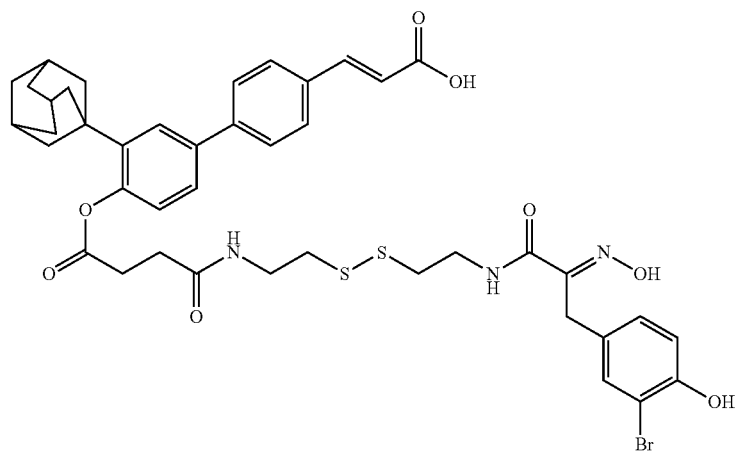 [SMILES: O=C(O)/C=C/c1ccc(-c2ccc(OC(=O)CCC(=O)NCCSSCCNC(=O)/C(Cc3ccc(O)c(Br)c3)=N/O)c(C34CC5CC(CC(C5)C3)C4)c2)cc1]
7
RC 1401
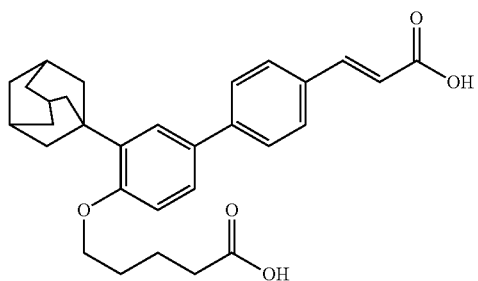 [SMILES: O=C(O)/C=C/c1ccc(-c2ccc(OCCCCC(=O)O)c(C34CC5CC(CC(C5)C3)C4)c2)cc1]

-continued
8
MIR002
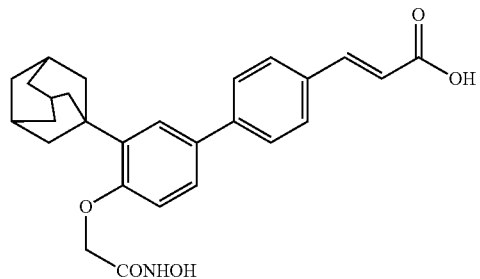
9
BIO 49
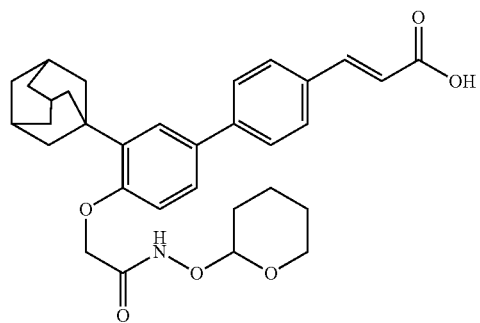 [SMILES: O=C(O)/C=C/c1ccc(-c2ccc(OCC(=O)NOC3CCCCO3)c(C34CC5CC(CC(C5)C3)C4)c2)cc1]
10
GEM 66
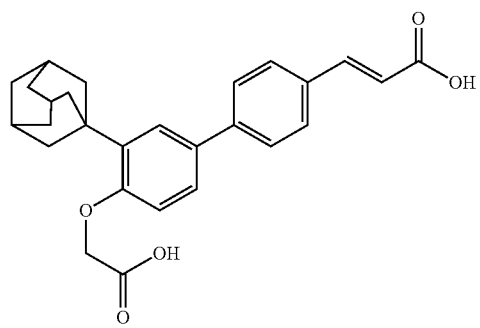 [SMILES: O=C(O)/C=C/c1ccc(-c2ccc(OCC(=O)O)c(C34CC5CC(CC(C5)C3)C4)c2)cc1]
11
GEM 57
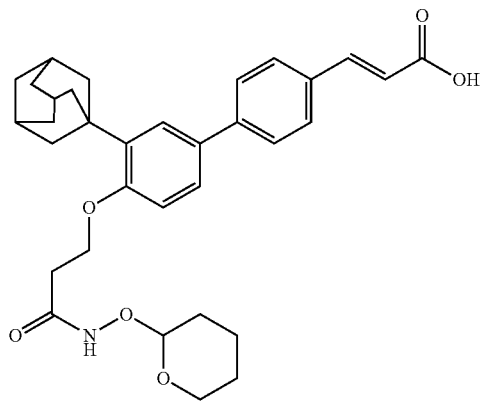 [SMILES: O=C(O)/C=C/c1ccc(-c2ccc(OCCC(=O)NOC3CCCCO3)c(C34CC5CC(CC(C5)C3)C4)c2)cc1]

-continued
12
GEM 60
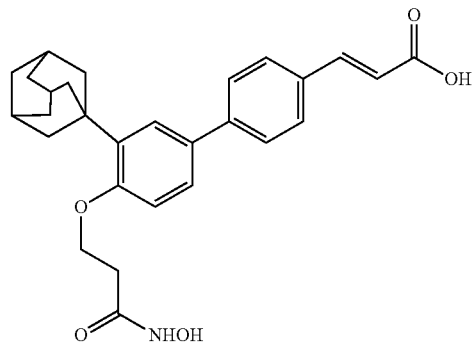
13
GEM 59
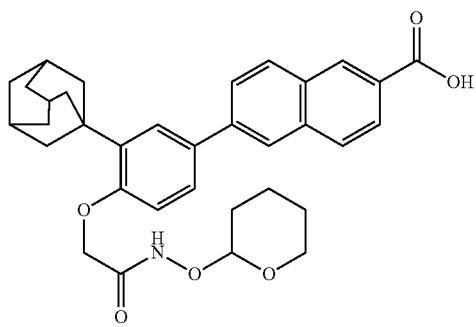 [SMILES: O=C(COc1ccc(-c2ccc3cc(C(=O)O)ccc3c2)cc1C12CC3CC(CC(C3)C1)C2)NOC1CCCCO1]
14
GEM 61
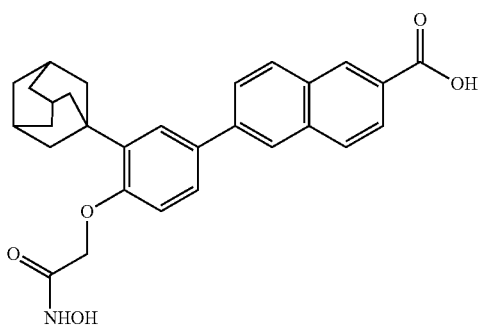
15
BIO 4
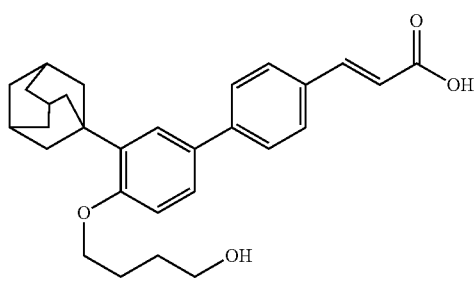 [SMILES: O=C(O)/C=C/c1ccc(-c2ccc(OCCCCO)c(C34CC5CC(CC(C5)C3)C4)c2)cc1]
16
GEM 95
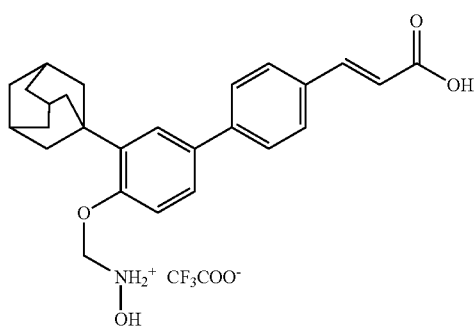

-continued
17
GEM 93
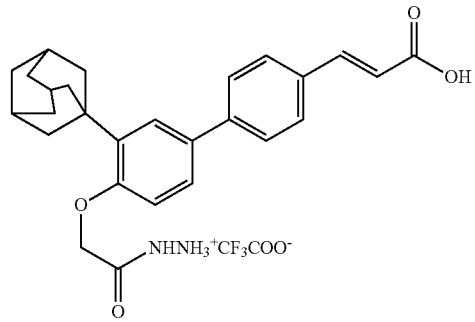
18
GEM 103
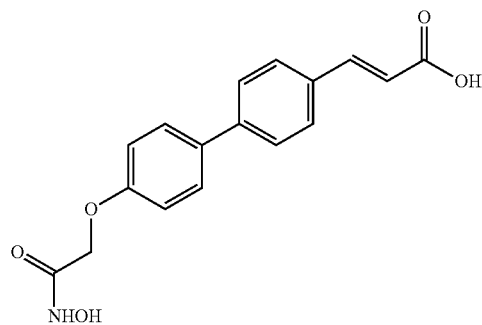
19
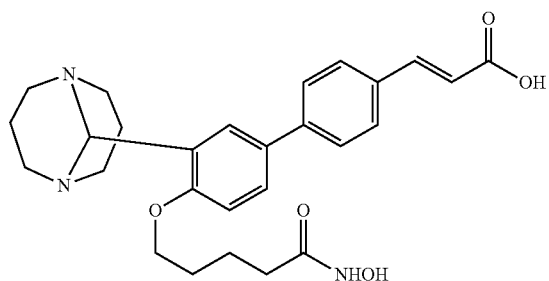
20
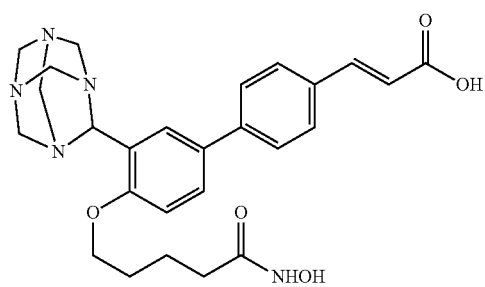
21
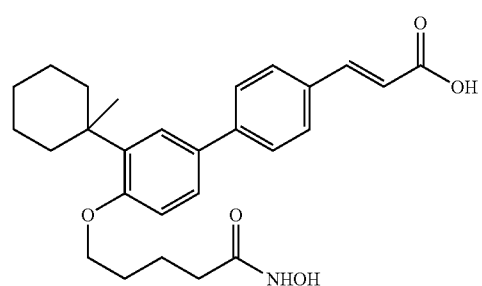

22 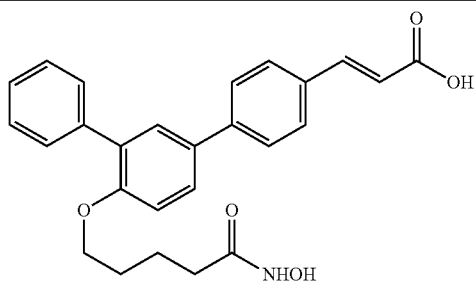

23 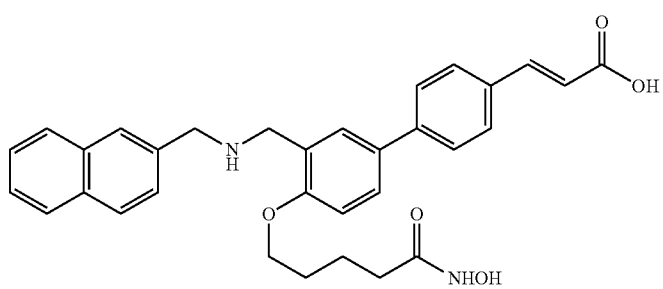

24 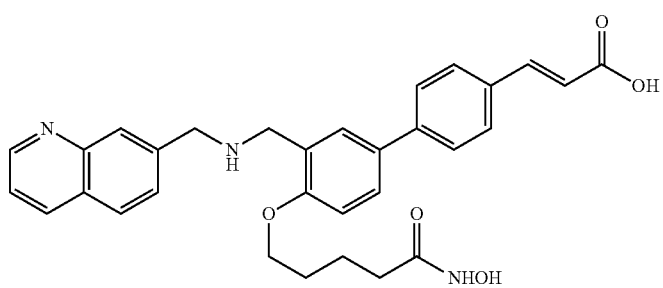

25 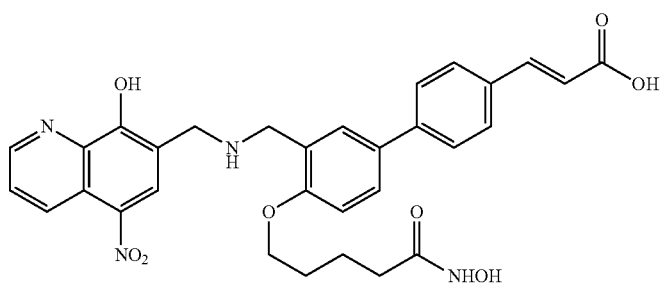

A process for the preparation of the compound of formula (I) is also within the scope of the present invention.

The compounds of the present invention can be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (Protective Groups in Organic Synthesis, 4th Edition, Wiley-Interscience (2006)).

Also, the skilled in the art can easily alter the reagents and reaction conditions exemplified in the schemes below to include any combination of substituents as defined above. Also, the skilled artisan can easily use interchangeable steps for each synthetic process and incorporate isolation and/or purification steps as deemed necessary.

Starting materials useful for the preparing the compounds of the invention and intermediates therefor, are commercially available or can be prepared by well known synthetic methods.

The final products obtained by the synthesis described below may be purified using techniques commonly known to one skilled in the art such as preparatory chromatography, thin-layer chromatography, HPLC, or crystallization.

Exemplary processes for the synthesis of the compounds of the invention are herein described.

Compounds of formula (I) wherein $R_5$ is 1-adamantyl can be obtained for example with a Suzuki-Miyaura reaction (Miyaura, N.; Suzuki, A. Chem. Rev. (1995), 95, 2457; Mora, M. et al. Curr. Org. Chemistry (2012), 16, 1128-1150; Heravi, M. et al. Tetrahedron (2012), 68, 9145-9178; Alonso, F. et al. Tetrahedron (2008), 64, 3047-3101) between 2-adamantan-1-yl-4-bromophenol (A) (Charpentier, B. et al. J. Med. Chem. (1995), 38, 4993-5006) or an ether (Tribulovich, V. G. et al., Russian J. Gen. Chem. 80(4), 868-869; 2010) or a silylderivative thereof, with a suitable boronate (B) where $R_4$ is O-alkyl in presence of Pd-tetrakis (triphenylphosphine) and 2M sodium or potassium carbonate, or dichloro(diphenylphosphinoferrocene) palladium·dichloromethane and potassium acetate, or a similar Pd catalyst with a similar base, in a solvent such as dimethoxyethane and ethanol, at temperatures from 25° C. to 80° C. (scheme 1).

Esters (B) can be prepared from the corresponding halide and bis(pinacolato)diboron in presence of $PdCl_2(dppf)$ and KOAc. (Giroux, A. et al. Tetrahedron Letters, (1997), 41, 3841-3844).

Alternatively, the corresponding boronic acids can be prepared by metal-halogen exchange of the corresponding halide, quenching with a trialkoxyborate reagent, and aqueous workup to provide the boronic acids (Miyaura, N. et al., Chem. Rev., (1995), 95, 2457).

The esters (C) thus obtained can be hydrolyzed for example with $LiOH·H_2O$ in $THF/H_2O$ to obtain the corresponding acids or reacted with suitable reagents (e.g. $NH_2OH$ or O-alkylhydroxylamines or amines) to give compounds containing the desired $COR_4$ group wherein $R_4$ has the meanings defined above, following well known procedures of organic synthesis.

The protecting group (e.g. tertbutoxycarbonyl), if present, can be eliminated by the common procedures known in the art. For example, it can be eliminated by treatment with trifluoroacetic acid in dichloromethane at T from 0° C. to room T.

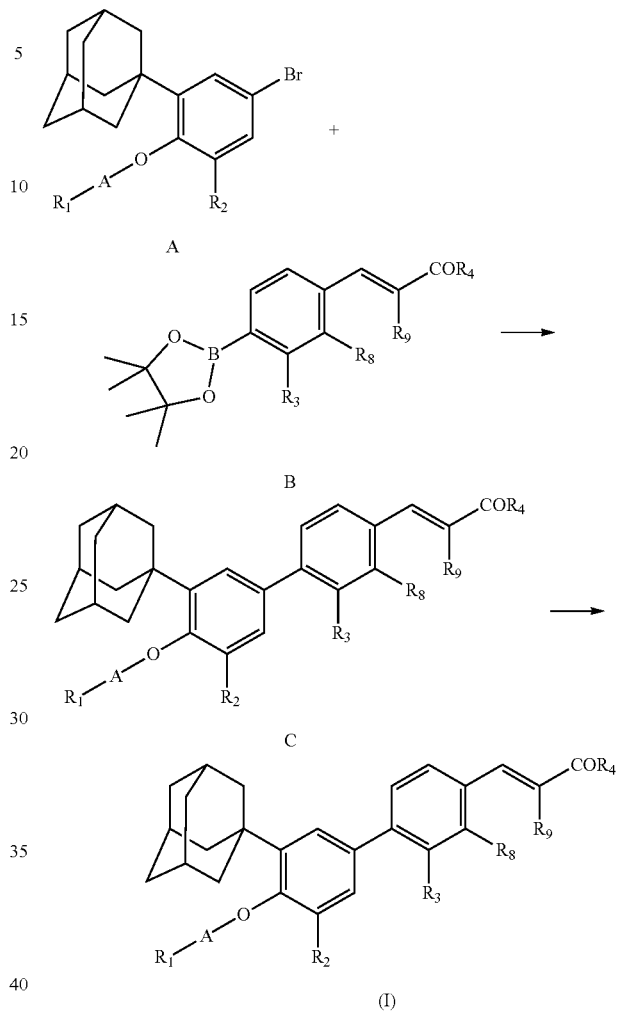

The same or similar reaction conditions hold for compounds of structure "A" of scheme 1 where $R_5$ is alkyl, cycloalkyl, azacycloalkyl, oxacycloalkyl, aryl, heteroaryl.

Compounds of general formula "A" where $R_2$ is different from H can be obtained for example by alkylation (Cincinelli et al. Bioorg. Med. Chem. 2007, 15, 4863) of compounds D (Cincinelli R. et al. J. Med. Chem. 2005, 48, 4931-4946), followed by reaction with bis(pinacolato)diboron in presence of $PdCl_2(dppf)$ and KOAc. (Giroux, A. et al. Tetrahedron Letters, (1997), 41, 3841-3844) (scheme 2).

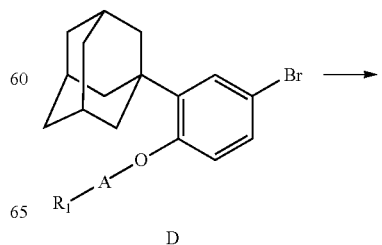

-continued

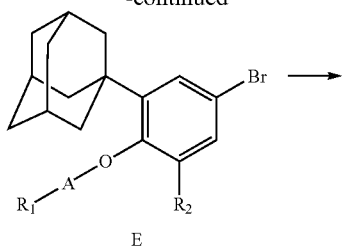
E

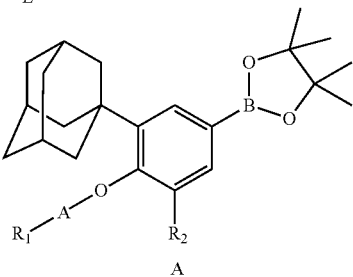
A

The same or similar reaction conditions hold for compounds of structure "D" of scheme 2 where $R_5$ is alkyl, cycloalkyl, azacycloalkyl, oxacycloalkyl, aryl, heteroaryl.

Compounds having further meanings of $R_2$ according to the present invention can be easily obtained by the skilled person based on the above exemplary procedures according to the standard methods of organic synthesis and common general knowledge in the field.

Compounds of general formula "B" can be obtained for example by formylation (Bhatt, S. et al. Tetrahedron Letters, 50(42), 5823-5826; 2009) or amidoalkylation (Cincinelli et al. Bioorg. Med. Chem. 2007, 15, 4863) or with other well known methods of organic synthesis, of commercially available p-bromophenol, followed by Heck coupling with a suitable acrylate (Heck, R. F. Organic Reactions, Vol. 27, 1982). The obtained 3-substituted-4-hydroxycinnamic esters can be converted into the corresponding triflates (B) by standard methods (e.g. Cincinelli, R. et al Eur. J. Med. Chem., 79, 251-259; 2014; Dallavalle, S. et al. J. Med. Chem. (2005), 48, 4931-4946) (route a, scheme 3).

Alternatively, compounds of general formula "B" where $R_3$ is for example heterocycloalkyl can be obtained by Mannich reaction of suitable 4-hydroxycinnamates with paraformaldehyde and amines (Nakano, H. J. Med. Chem., (2012), 55, 5151-5164), followed by conversion into the corresponding triflates (B) by standard methods (route b, scheme 3).

Scheme 3

Route a

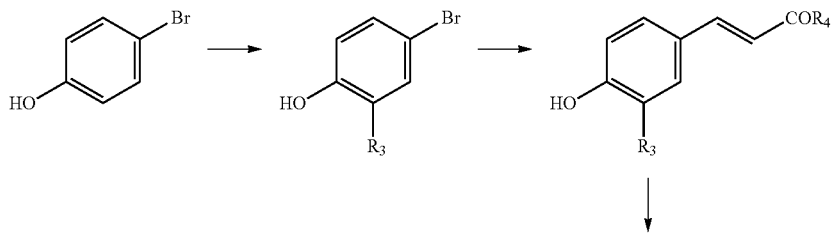

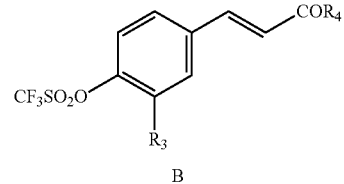
B

Route b

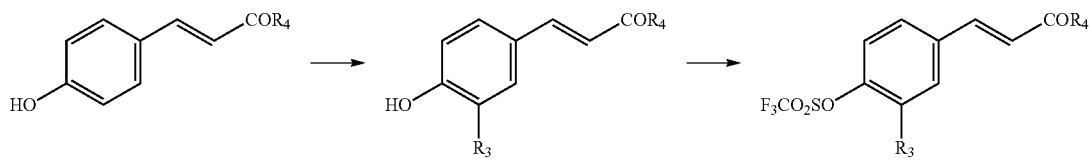

Compounds of formula (I) where $R_3$ is a formyl group can be converted into the corresponding oximes or alkyloximes (Cullen, M. et al. J. Med. Chem. (2007), 50, 4854-4867), alcohols (Kostikov, A. P. et al. J. Org. Chem. (2007), 72, 9190-9194), amides (Xu, J. E. J. Org. Chem. (2004), 15, 3244-3253), alkenes according to standard methods of organic synthesis.

Compounds having further meanings of $R_3$ according to the present invention can be easily obtained by the skilled person based on the above exemplary procedures according to the standard methods of organic synthesis and common general knowledge in the field.

This reaction scheme can be applied not only to esters, but also to other compounds where $R_4$ is different from O-alkyl.

Compounds of general formula (I) can be converted into other compounds of general formula (I) via suitable transformations.

For example, compounds of formula C where $R_1$ is OH, can be converted into compounds where $R_1$ has the meanings above defined by reactions of alkylation, followed by further transformations according to general methods of organic synthesis.

For example, compounds of formula (I) where $R_1$ is CONHOH, COOH, COO-alkyl, CONHOalkyl, CONHNH$_2$, CONH-aryl, $R_2$ and $R_3$ are H and $R_8$ and $R_9$ are H, can be obtained by conversion of acid F (Cincinelli R. et al. J. Med. Chem. 2005, 48, 4931-4946) into a suitable ester G (for example, a tert-butyl ester, Giannini, G. et al. Bioorg. Med. Chem. (2012), 20(7), 2405-2415), followed by alkylation with suitable alkyl bromoalkylcarboxylates (Naik, Ravi et al. J. Med. Chem. (2012), 55, 10564-10571) to obtain the O-substituted intermediates H. The esters (H) thus obtained can be hydrolyzed with LiOH·H$_2$O in THF/H$_2$O to obtain the corresponding acids. Reaction with suitable reagents (e.g. NH$_2$OH or O-alkylhydroxylamines or amines) followed by treatment with TFA gives compounds containing the desired COR$_4$ group wherein $R_4$ has the meanings defined above. (Scheme 4).

Compounds of formula (I) where $R_1$ is CONHO-oxacycloalkyl can be obtained following the above described procedure by conversion of acid F into a suitable ester G (for example methyl ester) followed by alkylation with O-oxacycloalkylhydroxylamine to obtain the O-substituted intermediates H. The esters (H) thus obtained can be hydrolyzed with LiOH·H$_2$O in THF/H$_2$O to obtain the desired COR$_4$ group wherein $R_4$ has the meanings defined above.

Compounds of formula (I) where $R_1$ is CH$_2$OH or COCF$_3$, $R_2$ and $R_3$ are H and $R_8$ and $R_9$ are H, can be obtained by conversion of acid F (Cincinelli R. et al. J. Med. Chem. 2005, 48, 4931-4946) into a suitable ester G (for example, a methyl ester, Giannini, G. et al. Bioorg. Med. Chem. (2012), 20(7), 2405-2415), followed by alkylation with bromoalkylacetates or bromo-1,1,1-trifluoroalkyl-2-ones to obtain the O-substituted intermediates H. The esters (H) thus obtained can be hydrolyzed with LiOH·H$_2$O in THF/H$_2$O to obtain compounds containing the desired COR$_4$ group wherein $R_4$ has the meanings defined above. (Scheme 4).

Compounds of formula (I) where $R_1$ is CH$_2$SCOCH$_3$ or CH$_2$NHOH, $R_2$ and $R_3$ are H and $R_8$ and $R_9$ are H, can be obtained by conversion of acid F (Cincinelli R. et al. J. Med. Chem. 2005, 48, 4931-4946) into a suitable ester G (for example, a tert-buthyl ester, Giannini, G. et al. Bioorg. Med. Chem. (2012), 20(7), 2405-2415), alkylation with dibromoalkyls, reaction with potassium thioacetate or potassium methanthiolate or N, O-diBochydroxylamine followed by treatment with TFA. (Scheme 4). Compounds of formula (I) where $R_1$ is CH$_2$SH can be obtained following the above procedure by final treatment of intermediate H with $R_1$=CH$_2$SCOCH$_3$ with LiOH·H$_2$O in THF/H$_2$O.

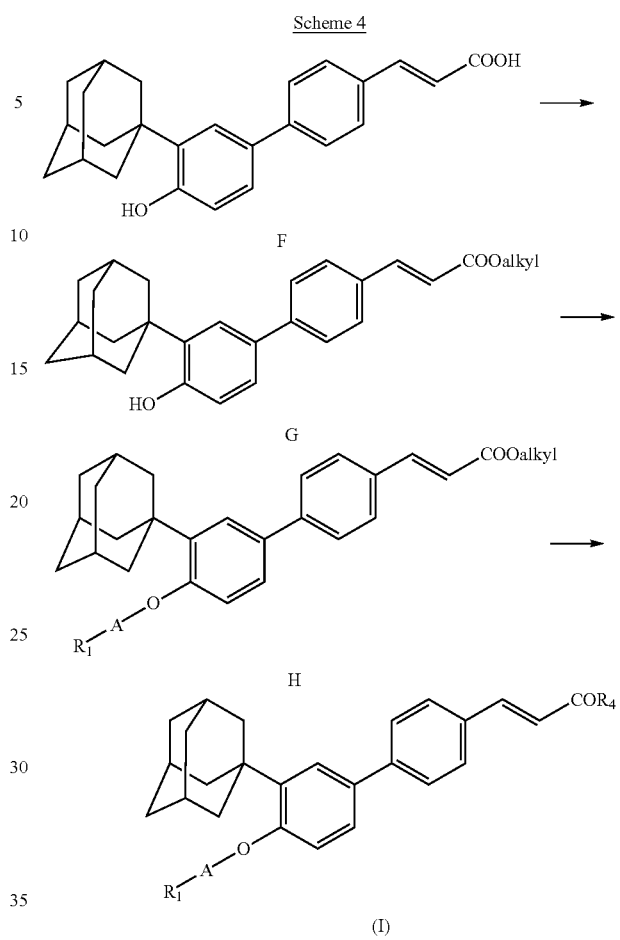

The same or similar reaction conditions hold for compounds of structure "F" of scheme 4 where $R_5$ is alkyl, cycloalkyl, azacycloalkyl, oxacycloalkyl, aryl, heteroaryl. Compounds having further meanings of $R_1$ or A-$R_1$ according to the present invention can be easily obtained by the skilled person based on the above exemplary procedures and according to the standard methods of organic synthesis and common general knowledge in the field.

Compounds of formula (M) where $R_2$ and $R_3$ are H and $R_5$ is alkylaminomethyl, arylakylaminomethyl, heteroarylalkylaminomethyl can be prepared starting from the esters J (Dallavalle S. et al. Eur. J. Med. Chem. (2009), 44(5), 1900-1912) via a Mannich reaction with formaldehyde and amines BNH$_2$, where B is alkyl, arylakyl, or heteroarylalkyl, optionally substituted with OH, Oalkyl, halogen, NO$_2$ and/or NH$_2$ depending on the desired $R_5$, as described for example by Šosič et al. J. Med. Chem. 2013, 56, 521-533. (Scheme 5)

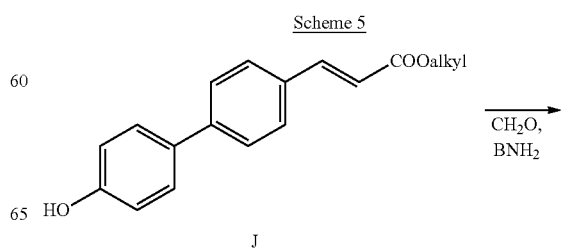

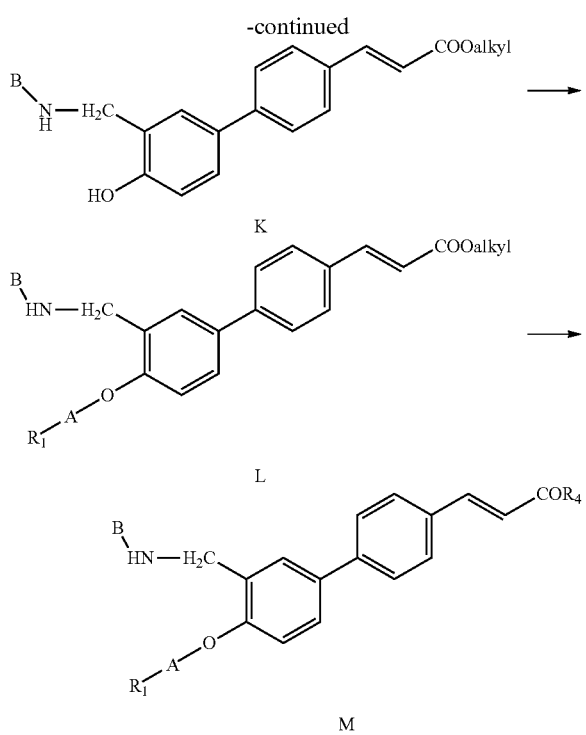

These esters can be transformed into esters L, then into compounds M following the procedures described in Scheme 4. In these transformations, the NH group of BNHCH$_2$ may be protected and deprotected according to the current procedures of organic synthesis.

In all the transformations above mentioned, every possibly interfering group can be protected and later deprotected according to standard procedures of organic chemistry, as described e.g. in P. G. M. Wuts and T. W. Greene "Greene's Protective Groups in Organic Synthesis", J. Wiley & Sons, Inc., 4rd Ed., 2006.

All the transformations above described are only exemplary synthetic procedures already known in organic chemistry and well known to the experts in the field.

Any variation or combination of substituents of compounds of formula (I) which is within the scope of the present invention and is not explicitly shown or described in the above processes, can be easily obtained starting from the exemplary processes described above with suitable modifications, for example in the starting compounds or reagents, that are well-known within the knowledge of the skilled person in the field of organic chemistry. Reference can be made, for example, to the handbook "March's Advanced Organic Chemistry, Reactions, Mechanism and structures.", Michael B. Smith, Jerry March, last edition.

It has been found that compounds of formula (I) are endowed with anti-proliferative activity and they are able to reduce tumor mass. Therefore, they can be advantageously used in the treatment of many cancer diseases.

It has also been found that the compounds of the invention can have an antitumor activity also on tumor resistant to known chemotherapy drugs, such as adarotene.

Furthermore, in many tumors the overexpression of P-glycoprotein (PGP) drastically reduces the possibility, after oral administration, of absorption of several chemotherapeutic agents (i.e. Paclitaxel, doxorubicin etc.). It has been found that the compounds of the invention are not PGP substrates, therefore they can be advantageously administered to the patients via oral route.

A further object of the present invention relates to the use of a compound of formula (I) as a medicament, in particular for the treatment of tumours. When it is used for the treatment of tumors, the antitumoral activity can be of cytotoxic nature and/or apoptotic nature, and/or antiangiogenic nature.

In a preferred embodiment, the tumour is selected from the group consisting of sarcoma, carcinoma, carcinoid, mesothelioma, lymphoma, bone tumour, neuroendocrine tumour, lymphoid leukaemia, myeloid leukaemia, monocytic leukaemia, megakaryocytic leukaemia, acute promyelocytic leukaemia, Hodgkin's disease, lung tumour, hepatoma, mesothelioma and intracranial tumor, such as glioma.

A further object of the present invention is the use of a compound of formula (I) for the prevention and treatment of tumour metastasis.

In a further embodiment of the invention, the compound of formula (I) can be used for the treatment of a disease related to altered angiogenesis.

The skilled in the art, for example a physician, can identify and recognize if a disease is related to altered angiogenesis on the basis of its general knowledge in the field.

In particular, the compound of formula (I) can be used for the treatment of the following diseases: arthritic pathology, diabetic retinopathy, psoriasis and chronic inflammatory disease.

Another object of the present invention is a pharmaceutical composition containing at least one compound of formula (I) as an active ingredient, preferably in an amount such as to produce a significant therapeutic effect, together with pharmaceutically acceptable vehicle and/or excipients.

Such pharmaceutical compositions can be prepared by conventional methods and techniques which are common practice in the pharmaceutical industry, such as, for example, those illustrated in Remington's Pharmaceutical Science Handbook, Mack Pub. N.Y.—last edition.

The compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

The pharmaceutical compositions according to the invention can also contain one or more further active ingredients, in particular chemotherapeutic agents. Such agents can be any molecule which is commonly used in the treatment of tumors. The chemotherapeutic agent can be chosen among the known agents according to the general knowledge of the skilled person in the field. For example, said chemotherapeutic agent can be selected from the group consisting of cytotoxic agents, proteasome inhibitors, immunomodulatory drugs, topoisomerase inhibitors, kinase inhibitors and monoclonal antibodies, in particular directed towards highly expressed tumor associated antigens. Particularly preferred is a composition comprising a compound of formula (I) and a platinum-based chemotherapeutic agent, in particular cisplatin. Indeed, it has been found that such combination has a synergistic anti-tumoral activity.

According to the administration route chosen, the compositions will be in solid or liquid form, suitable for oral, parenteral or topical administration.

Generally, the compounds of this invention are administered in a "therapeutically effective amount". The amount of the compound actually administered will typically be determined by a physician, in the light of the relevant circumstances, including the condition to be treated, the chosen route of administration, the actual compound administered, drug combination, the age, body weight, and response of the individual patient, the severity of the patient's symptoms, and the like. For any compound, the therapeutically effective dose can be estimated initially either in cell culture assays or in animal models, usually mice, rats, guinea pigs, rabbits, dogs, or pigs. The animal model may also be used to determine the appropriate concentration range and route of administration. Such information can then be used to determine useful doses and routes for administration in humans. In calculating the Human Equivalent Dose (HED) it is recommended to use the conversion table provided in Guidance for Industry and Reviewers document (2002, U.S. Food and Drug Administration, Rockville, Maryland, USA).

Generally, an effective dose will be from 0.01 mg/kg to 100 mg/kg, preferably 0.05 mg/kg to 50 mg/kg. For any compound, the therapeutically effective dose can be estimated initially either in cell culture assays or in animal models, usually mice, rats, guinea pigs, rabbits, dogs, or pigs. The precise effective dose for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician.

Compositions may be administered individually to a patient or may be administered in combination with other agents, drugs or hormones. For example they can be used in combination with further active ingredients, such as for example anticancer drugs.

The medicament may also contain a pharmaceutically acceptable carrier, for administration of a therapeutic agent. Such carriers include antibodies and other polypeptides, genes and other therapeutic agents such as liposomes, provided that the carrier does not induce the production of antibodies harmful to the individual receiving the composition, and which may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles.

A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol.

Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The medicament of this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, intravaginal or rectal means.

The compositions for oral administration may take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include refilled, pre-measured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form. Dosage treatment may be a single dose schedule or a multiple dose schedule.

A further object of the invention is a process for the preparation of pharmaceutical compositions characterized by mixing one or more compounds of formula (I) with suitable excipients, stabilizers and/or pharmaceutically acceptable diluents.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About (use of the term "about") can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Example 1

3-[3'-Adamantan-1-yl-4'-(3-hydroxycarbamoyl-propoxy)-biphenyl-4-yl]-acrylic acid (1)

Step 1. 3-[3'-Adamantan-1-yl-4'-(3-ethoxycarbonyl-propoxy)-biphenyl-4-yl]-acrylic acid tert-butyl ester A mixture of 3-(3'-adamantan-1-yl-4'-hydroxy-biphenyl-4-yl)-acrylic acid tert-butyl ester (50 mg, 0.115 mmol), ethyl bromobutanoate (36 mg, 0.17 mmol), $K_2CO_3$ (48 mg, 0.345 mmol) in 1.4 ml of DMF was heated at 60-80° C. for 2 h, added with 12 mg of ethyl bromobutanoate and heated again for 6 h. Evaporation, taking up with EtOAc, washing with water, drying, evaporation and chromatography with hexane/EtOAc 9:1 gave 67 mg of the product, m.p. 148° C. $^1$H-NMR (300 MHz, CHCl$_3$-d): 7.79-7.46 (6H, m), 7.41 (1H, dd, J=1.8, 8.2 Hz), 6.94 (1H, d, J=8.2 Hz), 6.40 (1H, d, J=15.9 Hz), 4.28-4.01 (4H, m), 2.64 (2H, t, J=7.6 Hz), 2.30-2.03 (11H, m), 1.87-1.70 (6H, m), 1.56 (s, 9H), 1.30 (3H, t, J=7.3).

Step 2. 3-[3'-Adamantan-1-yl-4'-(3-carboxy-propoxy)-biphenyl-4-yl]-acrylic acid tert-butyl ester The above ester (59 mg, 0.11 mmol), was dissolved in 3.4 ml of aq. 50% THF, added with 14 mg (0.32 mmol) of LiOH.H$_2$O, and the mixture was left overnight in the dark. Evaporation of the solvent, taking up with EtOAc, washing with 1N H$_2$SO$_4$ (10 ml), drying and evaporation gave 43 mg (87%) of the product as a white solid, m.p.>280° C. $^1$H-NMR (300 MHz, CDCl$_3$): 7.37/1H, d, J=16.2 Hz), 7.33-7.26 84H, m), 7.24 (1H, d, J=2.1 Hz), 7.17 81H, dd, 2.1, 8.2 Hz), 6.69 (1H, d, J=8.2 Hz), 6.15 (1H, d J=16.2 Hz), 3.87 (2H, t, J=6.1 Hz), 2.47 (2H, t, J=7.3 Hz), 2.06-1.95 (2H, m), 1.94-1.83 (9H, m), 1.59-1.49 (6H, m) 1.31 (9H, s).

Step 3. 3-{3'-Adamantan-1-yl-4'-[3-(tetrahydro-pyran-2-yloxycarbamoyl)-propoxy]-biphenyl-4-yl}-acrylic acid tert-butyl ester A mixture of the above ester (48 mg, 0.093 mmol), HOBt (26 mg, 0.19 mmol), and WSC (37 mg, 0.19 mmol) in 1 ml of dry DMF is left 5 h at room T, then is added with 23 mg (0.19 mmol) of O-(tetrahydro-pyran-2-yl)-hydroxylamine, and left overnight. Evaporation and chromatography with hexane/EtOAc 6:4 gave 153 mg of the product, that was used for the following step without further purification. $^1$H-NMR (300 MHz, CDCl$_3$): 7.97 (1H, brs), 7.38 (1H, d, J=16.2 Hz), 7.34-7.28 (4H, m), 7.24 (1H, d, J=1.8 Hz), 7.17 (1H, dd, J=1.8, 8.2 Hz), 6.69 (1H, d, J=8.24 Hz), 6.14 (1H, d, J=16.2 Hz), 4.78-4.66 (1H, m), 3.86 (2H, t, J=5.8 Hz), 3.73-3.60 (1H, m), 3.43-3.30 (1H, m), 2.27-2.12 (2H, m), 2.09-1.97 (2H, m), 1.96-1.82 (9H, m), 1.67-1.48 (10H, m), 1.45-1.27 (11H, m)

Step 4. 3-[3'-Adamantan-1-yl-4'-(3-hydroxycarbamoyl-propoxy)-biphenyl-4-yl]-acrylic acid Into an ice-cooled solution of the above ester (41 mg, 0.07 mmol) in 1.4 ml of CH$_2$Cl$_2$ was dropped TFA (0.7 ml). The mixture was left 2 h at 0° C., then evaporated, to give 42 mg of a yellow solid, that was chromatographed with CH$_2$Cl$_2$:CH$_3$OH:H$_2$O 18:2:0.2 to give 14 mg (44%) of the product as a white solid m.p. 242° C. (dec). $^1$H-NMR (300 MHz, DMSO-d$_6$): 10.47 (1H, s), 8.75 (1H, brs), 7.76-7.54 (5H, m), 7.51 (1H, dd, J=1.8, 8.5 Hz), 7.43 (1H, d, J=1.8 Hz), 7.03 (1H, d, J=8.5 Hz), 6.53 (1H, d, J=16.2 Hz), 4.03 (2H, t, J=7.0 Hz), 2.68-2.55 (2H, m), 2.29-2.17 (2H, m), 2.16-1.95 (9H, m), 1.82-1.66 (6H, m).

Example 2

3-[3'-Adamantan-1-yl-4'-(4-hydroxycarbamoyl-butoxy)-biphenyl-4-yl]-acrylic acid (2)

Step 1. 3-[3'-Adamantan-1-yl-4'-(4-ethoxycarbonyl-butoxy)-biphenyl-4-yl]-acrylic acid tert-butyl ester A solution of 3-(3'-adamantan-1-yl-4'-hydroxy-biphenyl-4-yl)-acrylic acid tert-butyl ester (200 mg, 0.46 mmol) and of ethyl 5-bromovalerate (194 mg, 0.92 mmol) in 8 ml of DMF was added with $K_2CO_3$ (257 mg, 1.86 mmol) and heated 3.5 h at 80° C. in the dark. Evaporation and chromatography with hexane/EtOAc 9:1 gave 197 mg (76%) of the product, m.p. 127° C. $^1$H-NMR (300 MHz, CDCl$_3$) δ: 7.62 (1H, d, J=15.8), 7.58-7.53 (4H, m), 7.48 (1H, d, J=2.2 Hz), 7.41 (1H, dd, J=2.2, 8.4 Hz), 6.93 (1H, d, J=8.4), 6.38 (1H, d, J=15.8 Hz), 4.16 (2H, d, j=7.2), 4.08-4.00 (2H, m), 2.47-2.38 (2H, m), 2.24-2.06 (9H, m), 1.99-1.88 (4H, m), 1.84-1.74 (6H, m), 1.55 (9H, s), 1.27 (3H, t, J=7.2 Hz)

Step 2. 3-[3'-Adamantan-1-yl-4'-(4-carboxy-butoxy)-biphenyl-4-yl]-acrylic acid tert-butyl ester A solution of the above ester (170 mg, 0.3 mmol) in 9.6 ml of aq. 50% THF was added with 38 mg (0.31 mmol) of LiOH·H$_2$O and left 3 h. Evaporation, taking up with EtOAc, washing with 20 ml of 1N KHSO$_4$, extraction with EtOAc, drying the extract with Na$_2$SO$_4$, filtration and evaporation gave 136 mg (84%) of the product, m.p. 169° C. $^1$H-NMR (300 MHz, DMSO-d$_6$) δ: 12.06 (1H, bs), 7.76-7.61 84H, m) 7.57 (1H, d, J=15.9 Hz), 7.51 (1H, d, J=2.3, 8.6 Hz), 7.43 (1H, d, J=2.3 Hz), 7.05 (1H, d, J=8.6 Hz), 6.53 (1H, d, J=15.9 Hz), 4.03 (2H, t, J=5.9 Hz), 2.32 (2H, t, J=6.6 Hz), 2.17-1.99 (9H, m), 1.88-1.68 (10H, m), 1.49 (9H, s).

Step 3. 3-{3'-Adamantan-1-yl-4'-[4-(tetrahydro-pyran-2-yloxycarbamoyl)-butoxy]-biphenyl-4-yl}-acrylic acid tert-butyl ester A mixture of the above ester (130 mg, 0.245 mmol), HOBt (68 mg, 0.49 mmol), and WSC (37 mg, 0.19 mmol)

in 1 ml of dry DMF is left 3 h at room T, added again with 1 ml of DMF and 24 mg of WSC, left overnight, then added with 85 mg (1.22 mmol) of O-(tetrahydro-pyran-2-yl)-hydroxylamine HCl, and 123 (1.22 mmol) of triethylamine and left 3 h under nitrogen atmosphere and in the dark. Evaporation of the DMF, taking up with 3 ml of water, filtration and chromatography with $CH_2Cl_2:CH_3OH$ 195:5, and a second chromatography with $CH_2Cl_2:CH_3OH$ 190:10 gave 60 mg (45%) of the product as a white solid. $^1$H-NMR (300 MHz, DMSO-$d_6$) δ: 10.39 (1H, s), 8.71 (1H, s), 7.77-7.61 (4H, m), 7.58 (1H, d, J=16.0 Hz), 7.51 (1H, dd, J=2.2, 8.7 Hz), 7.43 (1H, d, J=2.2 Hz), 7.05 (1H, d, J=8.7 Hz), 6.53 (1H, d, J=16.0 Hz), 4.07-3.97 (2H, m), 2.18-1.98 ( )H, m), 1.86-1.66 (10H, m) 1.49 (9H, s).

Step 4. 3-[3'-Adamantan-1-yl-4'-(4-hydroxycarbamoyl-butoxy)-biphenyl-4-yl]-acrylic acid Into an ice-cooled solution of the above ester (52 mg, 0.095 mmol) in 1.9 ml of $CH_2Cl_2$ was dropped TFA (0.95 ml). The mixture was left 3 h at 0° C., under nitrogen and in the dark, then evaporated, to give 42 mg, 89%) of the product as a white solid m.p. 224° C. (dec). $^1$H-NMR (300 MHz, DMSO-$d_6$) δ: 13.38 (1h, bs), 7.78-7.55 (5H, m), 7.51 (1H, dd, J=2.2, 8.3 Hz), 7.43 (1H, d, J=2.2 Hz), 7.05 (1H, d, J=8.3 Hz), 6.54 (1H, d, J=15.7 Hz), 4.07-3.97 (2H, m), 2.22-1.98 (11H, m), 1.91-1.62 (10H, m).

Example 3

3-[3'-Adamantan-1-yl-4'-(7-hydroxycarbamoyl-heptyloxy)-biphenyl-4-yl]-acrylic acid (3)

Step 1. Tert-butyl 3-{3'-adamantan-1-yl-4'-[7-(tetrahydro-pyran-2-yloxycarbamoyl)-heptyloxy]-biphenyl-4-yl}-acrylate A mixture of tert-butyl 3-(3'-adamantan-1-yl-4'-hydroxy-biphenyl-4-yl)-acrylate (150 mg, 0.35 mmol), 8-bromo-octanoic acid (tetrahydro-pyran-2-yloxy)-amide (146 mg, 0.45 mmol), and $K_2CO_3$ (137 mg, 0.99 mmol) in 6 ml of dry acetonitrile was refluxed 12 hrs, then added with 1 ml of dry DMF and 80 mg of $K_2CO_3$ and again refluxed 5 hrs. Evaporation, filtration and drying gave a crude product, that was purified by chromatography with hexane/AcOEt 1:1 to give 100 mg of a white solid, m.p. 154-156° C., $^1$H-NMR (300 MHz, CDCl$_3$) δ: 8.16 (1H, br s), 7.45-7.67 (6H, m), 7.42, 1H, dd, J=8.24 and J=2.14 Hz), 6.34 (1H, d, J=8.24 Hz), 6.33 (1H, m, J=16.2 Hz), 4.96 (1H, br s), 3.89-4.07 (3H, m), 3.60-3.70 (1H, m), 2.07-2.24 (11H, m), 1.75-1.96 (12H, m), 1.51-1.74 (15H, m), 1.36-1.48 (4H, m).

Step 2. 3-[3'-Adamantan-1-yl-4'-(7-hydroxycarbamoyl-heptyloxy)-biphenyl-4-yl]-acrylic acid (23)

A solution of tert-butyl 3-{3'-adamantan-1-yl-4'-[7-(tetrahydro-pyran-2-yloxycarbamoyl)-heptyloxy]-biphenyl-4-yl}-acrylate (88 mg, 0.13 mmol) in 2.6 ml of $CH_2Cl_2$ was cooled in an ice bath, treated dropwise with 1.3 ml of TFA and stirred at room T for 30 min. Evaporation, and taking up with ether gave a white solid, that was washed with hexane to give 70 mg of the product, m.p. 177° C. (dec), $^1$H-NMR (300 MHz, DMSO-$d_6$) δ: 12.3 (1H, br s), 10.3 (1H, s), 8.66 (1H, brs), 7.56-7.77 (5H, m), 7.51, 1H, d, J=8.24 Hz), 7.43 (1H, s), 7.04 (1H, d, J=8.24 Hz), 6.53 (1H, m, J=16.2 Hz), 4.02 (2H, t, J=5.19 Hz), 2.01-2.18 (9H, m), 1.94 (2H, t, J=7.93 Hz), 1.67-1.87 (8H, m), 1.43-1.60 (4h, m), 1.19-1.42 (4H, m).

Example 4

2-(2-{4-[3-Adamantan-1-yl-4'-(2-carboxy-vinyl)-biphenyl-4-yloxy]-butyrylamino}-ethyldisulfanyl)-ethyl-ammonium; trifluoroacetate (4) (RC 1363)

Step 1. 3-[3'-Adamantan-1-yl-4'-(3-{2-[2-tert-butoxycarbonylamino-ethyldisulfanyl]-ethylcarbamoyl}-propoxy)-biphenyl-4-yl)-acrylic acid tert-butyl ester A mixture of 3-[3'-Adamantan-1-yl-4'-(3-carboxy-propoxy)-biphenyl-4-yl]-acrylic acid tert-butyl ester (80 mg, 0.155 mmol), HOBt (43 mg, 0.31 mmol), and WSC (61 mg, 0.31 mmol) in 0.84 ml of DMF was stirred for 5 h (a precipitate formed), then added with [2-(2-amino-ethyldisulfanyl)-ethyl]-carbamic acid tert-butyl ester (Biochem. Biophys, Res. Comm. 331, 1, 351-356) (the precipitate dissolves) and left overnight. Evaporation and chromatography with hexane/EtOAc 4:6 gave 99 mg (85%) of the product as a white solid, m.p. 79° C. $^1$H-NMR (300 MHz, CDCl$_3$): 7.62 (1H, d, J=16.0), 7.61-7.51 (4H, m), 7.48 (1H, d, J=2.3), 7.40 (1H, dd, J=2.3, 8.3), 6.93 (1H, d, J=8.3), 6.38 (1H, d, J=16.0), 6.42 (1H, bs), 4.94 (1H, bs), 4.08 (2H, t, J=6.1), 3.65-3.55 (2H, m), 3.49-3.38 (2H, m), 2.85 (2H, t, J=6.2), 2.76 (2H, t, J=6.9), 2.52 (2H, t, J=7.2), 2.32-2.20 (2H, m), 2.18-2.06 (9H, m), 1.85-1.74 (6H, m), 1.61-1.52 (9H, s), 1.45 (9H, s).

Step 2. 2-(2-{4-[3-Adamantan-1-yl-4'-(2-carboxy-vinyl)-biphenyl-4-yloxy]-butyrylamino}-ethyldisulfanyl)-ethyl-ammonium; trifluoroacetate A solution of the above ester (81 mg, 0.11 mmol) in 8.2 ml of dichloromethane was cooled with ice, then added with dropwise with 2 ml of TFA, and left at 0° C. under nitrogen, for 4 h. Evaporation gave 76 mg (100%) of the product, as a yellow solid, m.p 140° C. $^1$H-NMR (300 MHz, CH$_3$OH-d$_4$): 7.77 (6H, m), 7.51-7.40 (2H, m), 7.01 (1H, d J=8.5), 6.49 (1H, d, J 0 15.9), 4.09 (2H, t, J=6.2), 3.54 (2H, t, J=6.7), 3.28 (2H, t, J=6.7), 2.97 (2H, t, J=6.7), 2.87 (2H, t, J=6.7), 2.51 (2H, t, J=7.0), 2.26-2.14 (9H, m), 2.13-2.03 (2H, m), 1.89-1.77 (6H, m).

Example 5

3-{3'-Adamantan-1-yl-4'-[3-(2-{2-[3-(3-bromo-4-hydroxy-phenyl)-2-hydroxyimino-propionylamino]-ethyldisulfanyl}-ethylcarbamoyl)-propoxy]-biphenyl-4-yl}-acrylic acid. (RC 1338)

Step 1. (2-{2-[3-(3-Bromo-4-hydroxy-phenyl)-2-hydroxyimino-propionylamino]-ethyldisulfanyl}-ethyl)-carbamic acid tert-butyl ester A solution of 3-(3-bromo-4-hydroxy-phenyl)-2-hydroxy-imino-propionic acid (1.54 g, 5.62 mmol) in 34 ml of DMF was added with DCC (1.74 g, 8.43 mmol) and N·hydroxysuccinimide (0.99 g, 8.43 mmol) and left at room T for 3 h, then added with [2-(2-amino-ethyldisulfanyl)-ethyl]-carbamic acid tert-butyl ester, and left overnight at room T. Evaporation, cooling, addition of dichloromethane, filtration, evaporation and chromatography with $CH_2Cl_2$:

CH₃OH 95.5 gave 984 mg of the product, which was used without further purification. ¹H-NMR (300 MHz, CDCl₃): 7.47 (1H, d, J=1.8), 7.22 (1H, dd, J 0 1.8, 8.5), 6.89 (1H d J=8.5 Hz), 5.10 (1H, bs), 5.91 (1H, bs), 3.88 (2H, s), 3.71-3.57 (2H, m), 3.50-3.35 (2H, m), 2.93-2.68 (4H, m), 1.46 (9H, s).

Step 2. 2-{2-[3-(3-Bromo-4-hydroxy-phenyl)-2-hydroxyimino-propionylamino]-ethyldisulfanyl}-ethyl-ammonium; trifluoro-acetate A solution of the above compound (0.97 g, 1.9 mmol) in 61 ml of dichloromethane, under nitrogen, was added with 3.7 ml of TFA, and left 2 h at room T. Evaporation and chromatography with CH₂Cl₂:CH₃OH 90:10, then with CH₂Cl₂:CH₃OH 85:15, gave 938 mg of the product. ¹H-NMR (300 MHz, DMSO-d₆): 8.12 (1H, t, J=5.2 Hz), 7.28 (1H, d, J=1.8 Hz), 7.01 (1H, dd, J=1.8, 8.2 Hz), 6.83 (1H, d, J=8.2 Hz), 3.69 (2H, s), 3.49-3.39 (2H, m), 2.97 (2H, t, J=6.4 Hz), 2.87-2.78 (4H, m).

Step 3. 3-{3'-Adamantan-1-yl-4'-[3-(2-{2-[3-(3-bromo-4-hydroxy-phenyl)-2-hydroxyimino-propionylamino]-ethyldisulfanyl}-ethylcarbamoyl)-propoxy]-biphenyl-4-yl}-acrylic acid tert-butyl ester A mixture of 3-[3'-adamantan-1-yl-4'-(4-carboxy-propoxy)-biphenyl-4-yl]-acrylic acid tert-butyl ester (65 mg, 0.126 mmol), HOBt (35 mg, 0.25 mmol), and WSC (49 mg, 0.25 mmol) in 1 ml of DMF was stirred for 3 h (a white precipitate formed), added with a solution of 98 mg (0.19 mmol) of 2-{2-[3-(3-bromo-4-hydroxy-phenyl)-2-hydroxyimino-propionylamino]-ethyldisulfanyl}-ethyl-ammonium; trifluoroacetate in 0.9 ml of dry DMF, and left at room T under nitrogen, for 72 h. Evaporation and chromatography with CH₂Cl₂:CH₃OH 20:0.4 gave 71 mg of the product, as a mixture of syn and anti-oxime. ¹H-NMR (300 MHz, CDCl₃): 9.34 (1H, brs), 7.61 (1H, d, J=16.1 Hz), 7.56-7.51 (4H, m), 7.49-7.43 (2H, m), 7.37 (1H, dd, J=1.9, 8.2 Hz), 7.24-7.16 (2h, m), 6.90-6.84 (2h, m), 6.38 (1H, d, J=16.1), 6.2 (1H, t, J=5.9 Hz), 5.59 (1H, bs), 4.06 (2H, t, J=5.9), 3.86 (2H, s), 3.66-3.53 (4H, m), 2.87-2.76 (4H, m), 2.54 (2H, t, J=7.3), 2.32-2.20 (2H, m), 2.19-2.04 (9H, m), 1.86-1.70 (6H, m), 1.55 (9H, s).

Step 4. 3-{3'-Adamantan-1-yl-4'-[3-(2-{2-[3-(3-bromo-4-hydroxy-phenyl)-2-hydroxyimino-propionylamino]-ethyldisulfanyl}-ethylcarbamoyl)-propoxy]-biphenyl-4-yl}-acrylic acid A solution of the above ester (61 mg, 0.07 mmol) in 9 ml of dichloromethane was cooled in ice, then added dropwise with 1.5 ml of TFA, and left at room T for 4 h. Evaporation, and crystallization from dichloromethane/ether gave 46 mg of the product, m.p. 169° C. (dec). ¹H-NMR (300 MHz, DMSO-d₆): 12.32 (1H, bs), 11.84 (1H, s), 10.02 (1H, s), 8.15-7.99 (1H, m), 7.77-7.55 (5H, m), 7.49 81H, dd, J=1.7, 8.3), 7.42 (1H, d, J=1.7), 7.26 (1H, s), 7.07-6.94 (2H, m), 6.81 (1H, d, J=8.3), 6.51 (1H, d, J=16.1), 4.07-3.96 (2H, m), 3.66 (2H, s), 3.52-3.37 (4H, m), 2.85-2.72 (4H, m), 2.33 (2H, t, J=7.3), 2.18-1.99 (11H, m), 1.78-1.66 (6H, m).

Example 6

3-{3'-Adamantan-1-yl-4'-[3-(2-{2-[3-(3-bromo-4-hydroxy-phenyl)-2-hydroxyimino-propionylamino]-ethyldisulfanyl}-ethylcarbamoyl)-propionyloxy]-biphenyl-4-yl}-acrylic acid (6) (AB 514)

Step 1. 3-{3'-Adamantan-1-yl-4'-[3-(2-{2-[3-(3-bromo-4-hydroxy-phenyl)-2-hydroxyimino-propionylamino]-ethyldisulfanyl}-ethylcarbamoyl)-propionyloxy]-biphenyl-4-yl}-acrylic acid tert-butyl ester. (AB513)

A solution of succinic acid mono-[3-adamantan-1-yl-4'-(2-tert-butoxycarbonyl-vinyl)-biphenyl-4-yl] ester (70 mg) in 2 ml of DMF was added with 35 mg of WSC and 22 mg of HOBt, and left overnight at room T under a nitrogen atmosphere. Evaporation and chromatography with CH₂Cl₂:CH₃OH 20:1 gave 90 mg of the title product, ¹H NMR (300 MHz, CDCl₃): 7.61 (1H, d, J=15.9 Hz), 7.57-7.52 (5H, m), 7.44 (1H, d, J=2.5 Hz), 7.41-7.35 (1H, m), 7.18 (1H, dd, J=2.5, 8.7 Hz), 7.04 (1H, d, J=8.3 Hz), 6.86 (1H, d, J=8.3 Hz), 6.39 (1H, d, J=15.9 Hz), 3.85 (2H, s), 3.63-3.48 (4H, m), 3.05-2.96 (2H, m), 2.84-2.74 (4H, m), 2.72-2.60 (2H, m), 2.13-1.99 (9H, m), 1.84-1.69 (6H, m), 1.55 (9H, s).

Step 2. 3-{3'-Adamantan-1-yl-4'-[3-(2-{2-[3-(3-bromo-4-hydroxy-phenyl)-2-hydroxyimino-propionylamino]-ethyldisulfanyl}-ethylcarbamoyl)-propionyloxy]-biphenyl-4-yl}-acrylic acid. (AB514)

A solution of 3-{3'-adamantan-1-yl-4'-[3-(2-{2-[3-(3-bromo-4-hydroxy-phenyl)-2-hydroxyimino-propionylamino]-ethyldisulfanyl}-ethylcarbamoyl)-propionyloxy]-biphenyl-4-yl}-acrylic acid tert-butyl ester (75 mg) in 10 ml of dry dichloromethane was cooled at 0° C., added dropwise with 1.5 ml of TFA and stirred 3 h. Concentration and chromatography with CH₂Cl₂:CH₃OH 20:1, then with CH₂Cl₂:CH₃OH 10:1 gave a crude product, that was dissolved in a mixture of dichloromethane and methanol, then added with ethyl ether, to give a precipitate, that was filtered, to give 50 mg of the title product, m.p. 198-199° C. (dec), ¹H-NMR (300 MHz, DMSO-d₆): 11.92 (1H, bs), 9.63 (1H, bs), 8.19 (1H, t, J=5.8 Hz), 8.10 (1H, t, J=5.8 Hz), 7.17-7.47 (5H, m), 7.43-7.22 (3H, m), 7.08 (1H, d, J=8.5 Hz), 7.00 (1H, d, J=8.8 Hz), 6.90-6.81 (1H, m), 6.54-6.41 (1H, m), 3.68 (2H, s), 2.91-2.70 (6H, m), 2.58-2.52 (2H, m), 2.19--1.92 (9H, m), 1.82-1.67 86H, m).

Example 7

3-[3'-adamantan-1-yl-4'-(4-carboxy-butoxy)-biphenyl-4-yl]-acrylic acid (7)

TFA (0.77 mL) was dropped into a solution of 3-[3'-adamantan-1-yl-4'-(4-carboxy-butoxy)-biphenyl-4-yl]-acrylic acid tert-butyl ester (40 mg, 0.077 mmol) (in CH₂Cl₂ (2.44 mL) at 0° C. (see example 22, step 2). The resulting yellow solution was stirred 3 h at 0° C. Evaporation followed by crystallization from CH₂Cl₂ gave the title compound as a white solid, m.p. 274° C.; Yield 95%; R$_f$ 0.10 (MeOH, RP). ¹H-NMR (DMSO-d₆) δ: 12.05 (1H, brs); 7.75-7.60 (4H, m); 7.59 (1H d, J=15.8 Hz); 7.49 (1H, dd, J=8.6 Hz, J=2.1 Hz); 7.41 (1H, d, J=2.1 Hz); 7.03 (1H, d, J=8.6 Hz); 6.52 (1H, d, J=15.8 Hz); 4.01 (2H, t, J=5.5 Hz), 2.30 (2H, t, J=6.9 Hz); 2.15-1.99 (9H, m); 1.87-1.66 (10H, m).

Example 8

3-(3'-Adamantan-1-yl-4'-hydroxycarbamoyl-methoxybiphenyl-4-yl)-acrylic acid (MIR002) (8)

Step 1: 3-(3'-Adamantan-1-yl-4'-ethoxycarbonyl-methoxy-biphenyl-4-yl)-acrylic acid tert-butyl ester A solution of 3-(3'-Adamantan-1-yl-4'-hydroxybiphenyl-4-yl)acrylic acid tert-butyl ester (250 mg, 0.581 mmol) and $K_2CO_3$ (321 mg, 2.32 mmol) in anhydrous DMF (10 mL), was added with ethyl bromoacetate (200 mg, 1.16 mmol). The solution was stirred at 80° C. under nitrogen for 2h. Filtration of potassium carbonate, followed by evaporation and purification by flash chromatography with ETP/AcOEt 90:10 gave 224 mg of the title compound. Yield 75%. $R_f$ 0.31 (ETP/AcOEt 9:1). $^1$H-NMR (300 MHz, $CDCl_3$) δ: 7.61 (1H, d, J=16.1 Hz); 7.57-7.54 (4H, m); 7.50 (1H, d, J=2.4 Hz); 7.39 (1H, dd, J=2.4, 8.4 Hz); 6.80 (1H, d, J=8.4 Hz); 6.38 (1H, d, J=16.1 Hz); 4.67 (2H, s); 4.31 (2H, q, J=7.1 Hz); 2.26-2.05 (9H, m); 1.80 (6H, s); 1.54 (9H, m); 1.32 (3H, t, J=7.1 Hz).

Step 2: 3-(3'-Adamantan-1-yl-4'-carboxymethoxy-biphenyl-4-yl)acrylic acid tert-butyl ester A suspension of 3-(3'-adamantan-1-yl-4'-ethoxycarbonyl-methoxy-biphenyl-4-yl)-acrylic acid tert-butyl ester (191 mg, 0.370 mmol) in $THF/H_2O$ 1:1 (11.4 mL) was added with $LiOH \cdot H_2O$ (77.6 mg, 1.85 mmol). The mixture was stirred at room temperature overnight. Evaporation, addition of ethyl acetate, washing with $KHSO_4$ 1N, drying and evaporation gave 181 mg of the title compound. Yield: 100%. $R_f$ 0.23 ($CH_2Cl_2$:MeOH 19:1). $^1$H-NMR (300 MHz, DMSO-$d_6$) δ: 7.78-7.37 (7H, m); 6.93 (1H, d, J=8.6 Hz); 6.50 (1H, d, J=16.1 Hz); 4.71 (2H, s); 2.18-1.95 (9H, m); 1.73 (6H, s); 1.48 (9H, m).

Step 3: 3-(3'-Adamantan-1-yl-4'-hydroxycarbamoyl-methoxy-biphenyl-4-yl)acrylic acid tert-butyl ester A solution of 3-(3'-adamantan-1-yl-4'-carboxymethoxybiphenyl-4-yl)acrylic acid tert-butyl ester (153 mg, 0.313 mmol), WSC (92 mg, 0.470 mmol), N-hydroxysuccinimide (55.2 mg, 0.470 mmol) in anhydrous DMF (3.30 mol) was stirred at room temperature overnight, then hydroxylamine hydrochloride (109 mg, 1.57 mmol) and TEA (159 mg, 1.57 mmol) were added. After stirring at room temperature for 12 h, the solvent was evaporated and water (5 mL) was added. Filtration and purification by chromatography ($CH_2Cl_2$/MeOH 19:1) gave 84 mg of the title compound. Yield 53%. $R_f$ 0.54 ($CH_2Cl_2$:MeOH 19:1) $^1$H-NMR (300 MHz, DMSO-$d_6$) δ: 10.73 (1H, s); 9.02 (1H, s); 7.82-7.37 (7H, m); 6.98 (1H, d, J=8.8 Hz); 6.51 (1H, d, J=16.1 Hz); 4.47 (2H, s); 2.18-1.95 (9H, m); 1.73 (6H, s); 1.48 (9H, m).

Step 4: 3-(3'-Adamantan-1-yl-4'-hydroxycarbamoyl-methoxybiphenyl-4-yl)-acrylic acid A solution of 3-(3'-Adamantan-1-yl-4'-hydroxycarbamoylmethoxy-biphenyl-4-yl)acrylic acid tert-butyl ester (61 mg, 0.121 mmol) in $CH_2Cl_2$ dry (3.81 mL) was added with TFA (1.21 mL) and stirred at 0° C. for 2h under nitrogen. The solvent was evaporated, toluene (2×3 mL) was added and the solvent was removed by azeotropic distillation. Crystallization from $CH_2Cl_2$ gave 46 mg of the title compound as a white solid, m.p. 265° C.; Yield 85%; $R_f$ 0.10 ($CH_2Cl_2$:MeOH 18:2). $^1$H-NMR (300 MHz, DMSO-$d_6$) δ: 12.34 (1H, s); 10.77 (1H, s); 9.05 (1H, s); 7.81-7.31 (7H, m); 7.06-6.90 (1H, m); 6.52 (1H, d, J=16.5 Hz); 4.45 (2H, s); 2.22-1.99 (9H, m); 1.72 (6H, s).

Example 9

3-{3'-Adamantan-1-yl-4'-[(tetrahydropyran-2-yloxy-carbamoyl)-methoxy]-biphenyl-4-yl}-acrylic acid (9, BIO 49)

Step 1: 3-(3'-Adamantan-1-yl-4'-tert-butoxycarbonylmethoxy-biphenyl-4-yl)-acrylic acid methyl ester (GEM 63)

A mixture of 3-(3'-adamantan-1-yl-4'-hydroxy-biphenyl-4-yl)-acrylic acid methyl ester (Cincinelli R. et al. J. Med. Chem. 2003, 46, 909-912) (250 mg, 0.64 mmol), tert-butyl bromoacetate (252 mg, 1.29 mmol), $K_2CO_3$ (357 mg, 2.58 mmol) in 4.86 ml of DMF was heated at 80° C. for 1 h. $K_2CO_3$ was filtered, DMF evaporated and the residue was taken up with water. The solid precipitated was filtered and crystallized from diethyl ether to give 187 mg (71%) of product as white solid, m.p. 182° C., $R_f$ (Hexane/EtOAc 80:20) 0.53. $^1$H-NMR (300 MHz, $CHCl_3$-d): 7.72 (1H, d, J=16.3 Hz), 7.61-7.53 (4H, m), 7.50 (1H, d, J=2.62 Hz), 7.38 (1H, dd, J=8.56, 2.62 Hz), 6.77 (1H, d, J=8.56 Hz), 6.46 (1H, d, J=16.3 Hz), 4.57 (2H, s), 3.82 (3H, s), 2.25-2.06 (9H, m), 1.87-1.73 (6H, m), 1.51 (9H, s).

Step 2: 3-(3'-Adamantan-1-yl-4'-carboxymethoxy-biphenyl-4-yl)-acrylic acid methyl ester (BIO 47, GEM85)

Into an ice-cooled solution of 3-(3'-Adamantan-1-yl-4'-tert-butoxycarbonylmethoxy-biphenyl-4-yl)-acrylic acid methyl ester (158 mg, 0.314 mmol) in 2.94 ml of CH2Cl2 was dropped TFA (0.980 ml). The mixture was left 3 hrs at rt, then evaporated to give 109 mg (78%) of product as white solid, m.p. 218° C., Rf (CH2Cl2/MeOH 18:2) 0.40. 1H-NMR (300 MHz, DMSO-$d_6$): 7.79-7.62 (5H, m), 7.49 (1H, dd, J=8.80, 2.10 Hz), 7.43 (1H, d, J=2.10 Hz), 6.93 (1H, d, J=8.80 Hz), 6.65 (1H, d, J=16.6 Hz), 4.71 (2H, s), 3.72 (3H, s), 2.20-1.97 (9H, m), 1.84-1.64 (6H, m).

Step 3: 3-{3'-Adamantan-1-yl-4'-[(tetrahydro-pyran-2-yloxycarbamoyl)-methoxy]-biphenyl-4-yl}-acrylic acid methyl ester (BIO 48, GEM87)

Into an ice-cooled suspension of 3-(3'-Adamantan-1-yl-4'-carboxymethoxy-biphenyl-4-yl)-acrylic acid methyl ester (87 mg, 0.195 mmol) in 2 ml of dry DMF, under nitrogen, HBTU (74 mg, 0.195 mmol) and DIPEA (75.6 mg, 0.585 mmol) were added. After two minutes 24 mg (0.195 mmol) of O-(tetrahydro-pyran-2-yl)-hydroxylamine were added and the mixture was left overnight at rt. DMF was evaporated, the residue was taken up with water and the white solid filtered. Purification by flash chromatography on silica gel with petroleum ether/EtOAc 60:40 gave 21 mg (88%) of product as white solid, m.p. 121° C., Rf (hexane/EtOAc 17:3) 0.18. 1H-NMR (300 MHz, DMSO-$d_6$): 11.3, 7.80-7.62 (5H, m), 7.50 (1H, dd, J=8.50, 2.20 Hz), 7.43 (1H, d, J=2.20 Hz), 6.95 (1H, d, J=8.50 Hz), 6.64 (1H, d, J=16.2 Hz), 4.91-4.84 (1H, m), 4.51 (2H, s), 4.00-3.88 (1H, m), 3.72 (3H, s), 3.57-4.46 (1H, m), 2.16-1.99 (9H, m), 1.81-1.45 (12H, m).

Step 4: 3-{3'-Adamantan-1-yl-4'-[(tetrahydro-pyran-2-yloxycarbamoyl)-methoxy]-biphenyl-4-yl}-acrylic acid (9, BIO 49)

To a solution of 3-{3'-Adamantan-1-yl-4'-[(tetrahydro-pyran-2-yloxycarbamoyl)-methoxy]-biphenyl-4-yl}-acrylic acid methyl ester (20 mg, 0.037 mmol) in 1.0 ml of aq. 50% THF was added with 8 mg (0.185 mmol) of LiOH·H2O and left overnight at rt. After evaporation of THF the remaining aqueous phase was acidified with KHSO4 1M. The precipitated white solid was filtered and dried to give 14 mg (69%) of the product as white solid, m.p. dec 284° C., Rf (CH$_2$Cl$_2$/MeOH 19:1) 0.30. 1H-NMR (300 MHz, DMSO-d$_6$): 12.3 (1H, brs), 11.4 (1H, s), 7.75-7.56 (5H, m), 7.49 (1H, dd, J=8.57, 2.05 Hz), 7.42 (1H, d, J=2.05 Hz), 6.95 (1H, d, J=8.57 Hz), 6.52 (1H, d, J=15.8 Hz), 4.91-4.85 (1H, m), 4.51 (2H, s), 4.01-3.87 (1H, m), 3.57-3.46 (1H, m), 2.20-1.98 (9H, m), 1.82-1.44 (12H, m).

Example 10

3-(3'-Adamantan-1-yl-4'-carboxymethoxy-biphenyl-4-yl)-acrylic acid (10)

Step 1: 3-(3'-Adamantan-1-yl-4'-carboxymethoxy-biphenyl-4-yl)-acrylic acid (10, GEM 66))

To a solution of 3-(3'-Adamantan-1-yl-4'-carboxymethoxy-biphenyl-4-yl)acrylic acid tert-butyl ester (Example 8, Step 2) 114 mg (0.233 mmol) in dichloromethane dry (7.34 mL) was added with TFA (2.33 mL) and stirred at 0° C. for 2 h. Evaporation of the solvent gave 79 mg (79%) of the product as white solid, m.p.>290° C., R$_f$ (CH$_2$Cl$_2$/MeOH 18:2) 0.21. $^1$H-NMR (300 MHz, DMSO-d$_6$): 12.6 (1H, brs); 7.76-7.63 (4H, m); 7.60 (1H, d, J=15.9 Hz); 7.48 (1H, dd, J=8.50, 2.12 Hz); 7.43 (1H, d, J=2.12 Hz); 6.93 (1H, d, J=8.50 Hz); 6.52 (1H, d, J=15.9 Hz); 4.71 (2H, s); 2.20-2.00 (9H, m); 1.83-1.66 (6H, m).

Example 11

3-{3'-Adamantan-1-yl-4'-[2-(tetrahydro-pyran-2-yloxycarbamoyl)-ethoxy]-biphenyl-4-yl}-acrylic acid (11, GEM 57)

Step 1: 3-[3'-Adamantan-1-yl-4'-(2-tert-butoxycarbonyl-ethoxy)-biphenyl-4-yl]-acrylic acid methyl ester (GEM 37)

To a solution of 3-(3'-Adamantan-1-yl-4'-hydroxy-biphenyl-4-yl)-acrylic acid methyl ester (615 mg, 1.58 mmol) in tert-butyl acrylate (22 mL) was added Na (18 mg, 0.79 mmol) at room temperature under nitrogen. The mixture was heated at 110° C. for 8 h. After cooling to room temperature, the resulting mixture was quenched with NaCl saturated solution and extracted with CH2Cl2. The combined organic extracts were dried over anhydrous Na2SO4 and evaporated under vacuum to give the crude product, which was purified by column chromatography on silica gel (hexane/ethyl acetate 85:15) to give 365 mg (45%) of product as white solid, m.p. 166° C., R$_f$ (hexane/AcOEt 85:15) 0.26. 1H-NMR (600 MHz, CHCl$_3$-d): 7.76 (1H, d, J=16.0 Hz), 7.69-7.55 (m, 4H), 7.50 (1H, d, J=2.23 Hz), 7.47 (1H, dd, J=8.45, 2.23 Hz), 6.95 (1H, d, J=8.45 Hz), 6.48 (1H, d, J=16.0 Hz), 4.31 (2H, t, J=5.72 Hz), 3.81 (3H, s), 2.80 (2H, t, J=5.72 Hz), 2.18-2.07 (9H, m), 1.84-1.78 (6H, m), 1.50 (9H, s), 1.48-1.43 (2H, m).

Step 2: 3-[3'-Adamantan-1-yl-4'-(2-carboxy-ethoxy)-biphenyl-4-yl]-acrylic acid methyl ester (GEM40)

Into an ice-cooled solution of the 3-[3'-Adamantan-1-yl-4'-(2-tert-butoxycarbonyl-ethoxy)-biphenyl-4-yl]-acrylic acid methyl ester (365 mg, 0.706 mmol) in 12.2 ml of CH$_2$Cl$_2$, under nitrogen, was dropped TFA (6.12 ml). The mixture was left 3 h at 0° C. then solvent was evaporated to give 293 mg of a solid that was purified by flash chromatography on silica gel (CH$_2$Cl$_2$/CH$_3$OH 15:5) to give 166 mg (51%) of the product as a white solid m.p. 230° C., R$_f$ (CH$_2$Cl$_2$/MeOH 195:5) 0.45. $^1$H-NMR (300 MHz, DMSO-d$_6$): 12.4 (1H, br s), 7.78-7.62 (5H, m), 7.50 (1H, dd, J=8.45, 2.30 Hz), 7.41 (1H, d, J=2.30 Hz), 7.04 (1H, d, J=8.45 Hz), 6.64 (1H, d, J=16.0 Hz), 4.21 (2H, t, J=5.73 Hz), 3.71 (3H, s), 2.75 (2H, t, J=5.73 Hz), 2.18-1.96 (9H, m), 1.82-1.69 (6H, m).

Step 3: 3-{3'-Adamantan-1-yl-4'-[2-(tetrahydro-pyran-2-yloxycarbamoyl)-ethoxy]-biphenyl-4-yl}-acrylic acid methyl ester (GEM42)

Into an ice-cooled suspension of 3-[3'-Adamantan-1-yl-4'-(2-carboxy-ethoxy)-biphenyl-4-yl]-acrylic acid methyl ester (146 mg, 0.317 mmol) in 3.22 ml of dry DMF, under nitrogen, HBTU (120 mg, 0.317 mmol) and DIPEA (123 mg, 0.951 mmol) were added. After two minutes 39 mg (0.317 mmol) of O-(tetrahydro-pyran-2-yl)-hydroxylamine were added and the mixture was left overnight at rt. DMF was evaporated, the residue was taken up with 5 ml of water and stirred at rt for 15 minutes. Than the white solid was filtered and purified by flash chromatography on silica gel (hexane/EtOAc 40:60) to give 165 mg (93%) of product as white solid, m.p. 169° C., R$_f$ (hexane/EtOAc 40:60) 0.34. 1H-NMR (300 MHz, aceton-d6): 10.28 (1H, br s), 7.77-7.67 (5H, m), 7.54-7.50 (2H, m), 7.10 (1H, d, J=8.73 Hz), 6.57 (1H, d, J=16.0 Hz), 4.96-4.90 (1H, m), 4.45-4.30 (2H, m), 4.02-3.92 (1H, m), 3.78 (3H, s), 3.57-3.46 (1H, m), 2.72 (2H, t, J=5.90 Hz), 2.21-2.15 (9H, m), 1.91-1.69 (8H, m), 1.65-1.50 (4H, m).

Step 4: 3-{3'-Adamantan-1-yl-4'-[2-(tetrahydro-pyran-2-yloxycarbamoyl)-ethoxy]-biphenyl-4-yl}-acrylic acid (11, GEM 57)

To a solution of 3-{3'-Adamantan-1-yl-4'-[2-(tetrahydro-pyran-2-yloxycarbamoyl)-ethoxy]-biphenyl-4-yl}-acrylic acid methyl ester (132 mg, 0.236 mmol) in 7.34 ml of aq. 50% THF was added with 49.5 mg (1.18 mmol) of LiOH·H$_2$O and left overnight at rt. After evaporation of THF the remaining aqueous phase was acidified with HCl 1M (1.2 ml). The precipitated white solid was filtered and dried to give 100 mg (78%) of the product, m.p. 150° C., R$_f$(CH$_2$Cl$_2$/MeOH 19:1) 0.19. $^1$H-NMR (300 MHz, DMSO-d$_6$): 12.35 (1H, br s), 11.14 (1H, s), 7.74-7.62 (4H, m), 7.60 (1H, d, J=16.1 Hz), 7.49 (1H, dd, J=8.51, 2.30 Hz), 7.41 (1H, d, J=2.30 Hz), 7.05 (1H, d, J=8.51 Hz), 6.52 (1H, d, J=16.1 Hz), 4.80-4.76 (1H, m), 4.30-4.14 (1H, m), 3.96-3.85 (1H, m), 2.56 (2H, t, J=5.55 Hz), 2.10-1.96 (9H, m), 1.81-1.58 (10H, m), 1.54-1.43 (2H, m).

Example 12

3-[3'-Adamantan-1-yl-4'-(2-hydroxycarbamoyl-ethoxy)-biphenyl-4-yl]-acrylic acid (12, GEM 60)

Step 1: 3-[3'-Adamantan-1-yl-4'-(2-hydroxycarbamoyl-ethoxy)-biphenyl-4-yl]-acrylic acid (12, GEM 60)

To a solution of 3-{3'-Adamantan-1-yl-4'-[2-(tetrahydropyran-2-yloxycarbamoyl)-ethoxy]-biphenyl-4-yl}-acrylic acid (Example 11, Step 4) (85 mg, 0.156 mmol) in dioxane (1 ml) at 0° C. under nitrogen were added 3.54 ml of HCl 4M solution in dioxane. The resulting mixture was stirred at 0° C. for 2h. After evaporation of the solvent the residue was purified by flash chromatography ($CH_2Cl_2$/MeOH/$H_2O$ 18.5:1.5:0.2) to give 43 mg (60%) of product as white solid, m.p. 242° C., $R_f$($CH_2Cl_2$/MeOH/$H_2O$ 18.5:1.5:0.2) 0.35. $^1$H-NMR (300 MHz, DMSO-$d_6$): 12.38 (1H, br s), 10.58 (1H, s), 8.78 (1H, br s), 7.74-7.62 (4H, m), 7.59 (1H, d, J=16.1 Hz), 7.49 (1H, dd, J=8.50, 2.05 Hz), 7.41 (1H, d, J=2.05 Hz), 7.05 (1H, d, J=8.50 Hz), 6.51 (1H, d, J=16.1 Hz), 4.21 (2H, t, J=5.87 Hz), one signal missing due to the overlap with solvent signal, 2.13-1.95 (9H, m), 1.83-1.62 (6H, m).

Example 13

6-{3-Adamantan-1-yl-4-[(tetrahydro-pyran-2-yloxycarbamoyl)-methoxy]-phenyl}-naphthalene-2-carboxylic acid (13, GEM 59)

Step 1: (2-Adamantan-1-yl-4-bromophenoxy)-acetic acid methyl ester (GEM 48)

A solution of 2-Adamantan-1-yl-4-bromophenol (500 mg, 1.63 mmol) and of ethyl bromoacetate (561 mg, 3.62 mmol) in 12.3 ml of DMF was added with $K_2CO_3$ (901 mg, 6.52 mmol) and heated 1 h at 80° C. DMF was evaporated and the residue was poured into water and extracted with ethyl acetate. The organic extracts were washed sequentially with water, brine, dried over $Na_2SO_4$ and concentrated. The residue was purified by flash chromatography (hexane/Ethyl acetate 95:5) to give 400 mg (62%) of the desired compound as a yellow solid, m.p. 98° C., $R_f$ (Hexane/Ethyl acetate 95:5) 0.39.

$^1$H-NMR (300 MHz, CDCl$_3$) δ: 7.33 (1H, d, J=2.54 Hz), 7.24 (1H, dd, J=8.65, 2.54 Hz), 6.58 (1H, d, J=8.65 Hz), 4.59 (2H, s), 4.28 (2H, q, J=7.15 Hz), 2.15-2.04 (9H, m), 1.84-1.71 (6H, m), 1.30 (3H, t, J=7.15 Hz).

Step 2: (2-Adamantan-1-yl-4-bromophenoxy)-acetic acid (GEM50)

To a solution of (2-Adamantan-1-yl-4-bromophenoxy)-acetic acid methyl ester (223 mg, 0.567 mmol) in 17.6 ml of aq. 50% THF was added LiOH·$H_2O$ (119 mg, 2.84 mmol) and the mixture was stirred at rt overnight. After evaporation of THF, HCl 2M (3 ml) was added and the white solid precipitated was filtered and dried to give 195 mg (94%) of the desired compound, m.p. 208° C., $R_f$(Hexane/Ethyl acetate 50:50) 0.20. $^1$H-NMR (300 MHz, DMSO) δ: 7.30 (1H, dd, J=8.82, 2.58 Hz), 7.18 (1H, d, J=2.58 Hz), 6.81 (1H, d, J=8.82 Hz), 4.64 (2H, s), 2.09-1.95 (9H, m), 1.79-1.63 (6H, m).

Step 3: 2-(2-Adamantan-1-yl-4-bromophenoxy)-N-(tetrahydropyran-2-yloxy)-acetamide (GEM 51)

Into an ice-cooled suspension of (2-Adamantan-1-yl-4-bromophenoxy)-acetic acid (175 mg, 0.479 mmol) in 4.87 ml of dry DMF, under nitrogen, HBTU (182 mg, 0.479 mmol) and DIPEA (186 mg, 1.44 mmol) were added. After two minutes 58.4 mg (0.0.479 mmol) of O-(tetrahydropyran-2-yl)-hydroxylamine were added and the mixture was left overnight at rt. DMF was evaporated, the residue was taken up with 5 ml of water and stirred at rt for 15 minutes. Then the white solid was filtered and purified by flash chromatography on silica gel (hexane/EtOAc 70:30) to give 176 mg (79%) of product as white solid, m.p. 134° C., $R_f$ (hexane/ethyl acetate 70:30) 0.37. $^1$H-NMR (300 MHz, CDCl$_3$) δ: 9.03 (1H, s), 7.35 (1H, d, J=2.52 Hz), 7.29 (1H, dd, J=8.72, 2.52 Hz), 6.70 (1H, d, J=8.72 Hz), 5.05-4.99 (1H, m), 4.60 (2H, s), 3.98-3.87 (1H, m), 3.66-3.57 (1H, m), 2.15-2.01 (9H, m), 1.94-1.70 (12H, m).

Step 4: 6-{3-Adamantan-1-yl-4-[(tetrahydropyran-2-yloxycarbamoyl)-methoxy]phenyl}-naphthalene-2-carboxylic acid methyl ester (GEM58, GEM54)

To a degassed 3.5:1 mixture of dimethoxyethane and water (2 ml), 2-(2-Adamantan-1-yl-4-bromophenoxy)-N-(tetrahydropyran-2-yloxy)-acetamide (104 mg, 0.224 mmol), (6-(methoxycarbonyl)naphthalene-2-boronic acid pinacol ester (91 mg, 0.291 mmol), PdCl$_2$(dppf) $CH_2Cl_2$ (8.20 mg, 0.0112 mmol) and sodium bicarbonate (56.5 mg, 0.672 mmol) were added under nitrogen. The mixture was heated for 1 h at 100° C., water was added and the mixture was extracted with $CH_2Cl_2$ (3×20 ml). The combined organic layers were dried over $Na_2SO_4$, filtered and evaporated. Purification by flash chromatography (hexane/ethyl acetate 60:40) gave 112 mg (88%) of the desired compound as white solid, m.p. 183° C., $R_f$(hexane/ethyl acetate 60:40) 0.19. $^1$H-NMR (300 MHz, DMSO-$d_6$) δ: 11.42 (1H, s), 8.62 (1H, d, J=1.79 Hz), 8.23 (1H, d, J=1.49 Hz), 8.17 (1H, d, J=8.73 Hz), 8.09 (1H, d, J=8.73 Hz), 7.97 (1H, dd, J=8.73, 1.49 Hz), 7.90 (1H, dd, J=8.73, 1.79 Hz), 7.63 (1H, dd, J=8.57, 2.20 Hz), 7.58 (1H, d, J=2.20 Hz), 7.01 (1H, d, J=8.57 Hz), 4.91-4.87 (1H, m), 4.53 (2H, s), 4.01-3.92 (1H, m), 3.90 (3H, s), 3.56-3.47 (1H, m), 2.21-2.00 (9H, m), 1.82-1.46 (12H, m).

Step 5: 6-{3-Adamantan-1-yl-4-[(tetrahydropyran-2-yloxycarbamoyl)-methoxy]-phenyl}-naphthalene-2-carboxylic acid (13, GEM59)

A suspension of 130 mg (0.228 mmol) of 6-{3-Adamantan-1-yl-4-[(tetrahydropyran-2-yloxycarbamoyl)-methoxy]phenyl}-naphthalene-2-carboxylic acid methyl ester in 9.12 ml of a 1M solution of NaOH in methanol was refluxed for 1h. The solvent was evaporated and water was added to the residue, then HCl 3M was slowly added. The solid formed was filtered and dried to give 100 mg (79%) of desired compound as white solid, m.p. 279° C., $R_f$(hexane/ethyl acetate 70:30) 0.24. $^1$H-NMR (300 MHz, DMSO-$d_6$) δ: 11.45 (1H, br s), 8.35 (1H, d, J=1.56 Hz), 8.05 (1H, d, J=1.83 Hz), 8.01 (1H, dd, J=8.71, 1.83 Hz), 7.95 (1H, d, J=8.71 Hz), 7.82 (1H, d, J=8.71 Hz), 7.71 (1H, dd, J=8.71, 1.83 Hz), 7.58-7.50 (2H, m), 7.01 (1H, d, J=8.45 Hz), 4.92-4.85 (1H, m), 4.50 (2H, s), 4.02-3.89 (1H, m), 3.56-3.44 (1H, m), 2.21-2.00 (9H, m), 1.82-1.44 (12H, m).

Example 14

6-(3-Adamantan-1-yl-4-hydroxycarbamoylmethoxyphenyl)-naphthalene-2-carboxylic acid (14, GEM 61)

Step 1: 6-(3-Adamantan-1-yl-4-hydroxycarbamoylmethoxy-phenyl)-naphthalene-2-carboxylic acid (14, GEM 61)

Into an ice-cooled solution of 6-{3-Adamantan-1-yl-4-[(tetrahydropyran-2-yloxycarbamoyl)-methoxy]-phenyl}-naphthalene-2-carboxylic acid (Example 13, Step 5) (75 mg, 0.135 mmol) in 4.25 ml of $CH_2Cl_2$ was dropped TFA (1.35 ml). The mixture was left 3 h at 0° C., under nitrogen, then evaporated. The residue was purified by flash chromatography on silica gel ($CH_2Cl_2$/MeOH/$H_2O$ 18.5:1.5:0.2) to give 32 mg (50%) of product as white solid, m.p.>280° C., $R_f$ ($CH_2Cl_2$/MeOH/$H_2O$ 18.5:1.5:0.2) 0.20. $^1$H-NMR (300 MHz, DMSO-$d_6$) δ: 13.03 (1H, br s), 10.79 (1H, s), 9.07 (1H, s), 8.58 (1H, d, J=1.72 Hz), 8.21 (1H, d, J=1.72 Hz), 8.14 (1H, d, J=8.50 Hz), 8.06 (1H, d, J=8.70 Hz), 7.96 (1H, dd, J=8.50, 1.72 Hz), 7.88 (1H, dd, J=8.70, 1.72 Hz), 7.63 (1H, dd, J=8.47, 2.25 Hz), 7.57 (1H, d, J=2.25 Hz), 7.03 (1H, d, J=8.47 Hz), 4.49 (2H, s), 2.20-2.00 (9H, m), 1.84-1.67 (6H, m).

Example 15

3-[3'-Adamantan-1-yl-4'-(hydroxyl-buthoxy)-biphenyl-4-yl]-acrylic acid (15)

Step 1: 3-[4'-(4-Acetoxy-butoxy)-3'-adamantan-1-yl-biphenyl-4-yl]-acrylic acid methyl ester (BIO3)

A mixture of 3-(3'-adamantan-1-yl-4'-hydroxy-biphenyl-4-yl)-acrylic acid methyl ester (Example 9, Step 1) (100 mg, 0.26 mmol), 4-bromobutyl acetate (67.4 mg, 0.34 mmol), $K_2CO_3$ (102 mg, 0.74 mmol) in 4.50 ml of DMF was heated at 80° C. for 2 h. $K_2CO_3$ was filtered, DMF evaporated and the residue was taken up with water. The mixture was diluted with ethyl acetate, washed with 1M HCl, water and brine. The organic phase was dried and the solvent evaporated. Purification by flash chromatography (petroleum ether/ethyl acetate 80:20) gave 98 mg (75%) of product as white solid, m.p. 157° C., $R_f$ (petroleum ether/EtOAc 80:20) 0.50. $^1$H-NMR (300 MHz, DMSO-$d_6$) δ: 7.76-7.60 (4H, m); 7.56 (1H, d, J=16.5 Hz); 7.48 (1H, dd, J=8.50, 2.14 Hz); 7.43 (1H, d, J=2.14 Hz); 6.95 (1H, d, J=8.50 Hz); 6.51 (1H, d, J=16.5 Hz); 4.84 (2H, s); 3.73 (3H, s); 4H missing due to the overlap with signal solvent; 2.20-1.98 (9H, m); 1.84-1.65 (6H, m); 1.47 (7H, s).

Step 2: 3-[3'-Adamantan-1-yl-4'-(hydroxyl-buthoxy)-biphenyl-4-yl]-acrylic acid (15, BIO 5)

The above ester (30 mg, 0.06 mmol) was suspended in 3 mL of a solution of 0.7 N NaOH in methanol and the mixture was refluxed for 10 h. after evaporation of methanol, the residue was treated with water, acidified with 1M HCl, and the precipitate was filtered. Crystallization from isopropyl ether gave 10 mg (37%) of the pure product as white solid, m.p. 208° C., $R_f$ (petroleum ether/EtOAc 50:50) 0.15. $^1$H-NMR (300 MHz, DMSO-$d_6$) δ: 7.74-7.61 (4H, m); 7.59 (1H, d, J=16.5 Hz); 7.49 (1H, dd, J=8.80, 2.11 Hz); 7.41 (1H, d, J=2.11 Hz); 7.03 (1H, d, J=8.80 Hz); 6.51 (1H, d, J=16.5 Hz); 4.49 (1H, brs); 4.02 (2H, t, J=6.38 Hz); 3.48 (2H, t, J=6.38 Hz); 2.16-2.20 (9H, m); 1.90-1.78 (2H, m); 1.77-1.59 (8H, m).

Example 16

3-(3'-Adamantan-1-yl-4'-hydroxyaminomethoxy-biphenyl-4-yl)-acrylic acid trifluoroacetate (16, GEM 95)

Step 1: 3-[3'-Adamantan-1-yl-4'-(2-bromo-ethoxy)-biphenyl-4-yl]-acrylic acid tert-butyl ester A solution of 3-(3'-Adamantan-1-yl-4'-hydroxybiphenyl-4-yl)acrylic acid tert-butyl ester (470 mg, 1.09 mmol) and 1,2-dibromoethane (410 mg, 2.18 mmol) in 2.20 ml of dry acetone was added with $K_2CO_3$ (301 mg, 2.18 mmol) and heated 15 h at reflux. $K_2CO_3$ was filtered and the solvent evaporated. The residue was poured into water and extracted with ethyl acetate. The organic extracts were dried over $Na_2SO_4$ and concentrated. The residue was purified by flash chromatography (hexane/Ethyl acetate 90:10) to give 104 mg (18%) of the desired compound as a white solid, m.p. 177° C., $R_f$ (Hexane/Ethyl acetate 90:10) 0.16. $^1$H-NMR (300 MHz, DMSO-$d_6$) δ: 7.76-7.60 (4H, m); 7.55 (1H, d, J=16.1 Hz); 7.50 (1H, dd, J=8.50, 2.14 Hz); 7.44 (1H, d, J=2.14 Hz); 7.02 (1H, d, J=8.50 Hz); 6.51 (1H, d, J=16.1 Hz); 4.42-4.35 (2H, m); 3.93-3.86 (2H, m); 2.21-2.00 (9H, m); 1.84-1.67 (6H, m); 1.47 (9H, s).

Step 2: tert-butyl 3-(3'-Adamantan-1-yl)-4'-(2-((tert-butoxycarbonyl)((-tert-buthoxycarbonyl)oxy)amino)ethoxy)-[1,1'-biphenyl]-4-yl)-acrylate To a suspension of sodium hydride (60% in mineral oil, 10 mg, 0.250 mmol) in 0.5 mL of DMF, N,O-diBoc-hydroxylamine (55.6 mg, 0.230 mmol) was added. The mixture was stirred for 30' at 0° C. then a solution of 3-[3'-Adamantan-1-yl-4'-(2-bromo-ethoxy)-biphenyl-4-yl]-acrylic acid tert-butyl ester (103 mg, 0.192 mmol) in 2 mL of DMF was slowly added. After having stirred at room temperature overnight, DMF was evaporated, the residue was poured into saturated solution of $NH_4Cl$ and extracted with ethyl acetate. The organic phase was dried and evaporated. Purification by flash chromatography (Hexane/Ethyl acetate 90:10) gave 109 mg (81%) of the desired compound as white solid; m.p. 165° C., $R_f$ (Hexane/Ethyl acetate 90:10) 0.26. $^1$H-NMR (300 MHz, CDCl$_3$) δ:7.61 (1H, d, J=16.1 Hz); 7.57.7.50 (4H, m); 7.47 (1H, d, J=2.21 Hz); 7.39 (1H, dd, J=8.46, 2.21 Hz); 6.93 (1H, d, J=8.46 Hz); 6.38 (1H, d, J=16.1 Hz); 4.27-4.17 (2H, m); 4.16-4.01 (2H, m); 2.22-2.02 (9H, m), 1.86-1.70 (6H, m); 1.54 (9H, s); 1.52 (9H, s); 1.49 (9H, s).

Step 3: 3-(3'-Adamantan-1-yl-4'-hydroxyaminomethoxy-biphenyl-4-yl)-acrylic acid trifluoroacetate (16, GEM 95)

Into an ice-cooled solution of the above ester (84 mg, 0.122 mmol) in 1.14 ml of $CH_2Cl_2$ was dropped TFA (0.381 ml). The mixture was left 2 h at 0° C., under nitrogen, then evaporated. Crystallization from diethyl ether gave 56 mg (84%) of product as white solid, m.p. 224° C., $^1$H-NMR (300 MHz, DMSO-$d_6$) δ: 10.4 (2H, brs); 8.84 (1H, brs); 7.76-7.62 (4H, m); 7.60 (1H, d, J=16.2 Hz); 7.52 (1H, dd, J=8.60, 2.01 Hz); 7.43 (1H, d, J=2.01 Hz); 7.07 (1H, d, J=8.60 Hz); 6.52 (1H, d, J=16.2 Hz); 4.21 (2H, t, J=5.61 Hz); 3.42-3.31 (2H, m); 2.18-1.99 (9H, m); 1.79-1.67 (6H, m).

Example 17

3-(3'-adamantan-1-yl-4'-hydrazinocarbonylmethoxy-biphenyl-4-yl)-acrylic acid trifluoroacetate (17, GEM 93)

Step 1: 3-(3'-Adamantan-1-yl-4'-hydrazinocarbonyl-methoxy-biphenyl-4-yl)-acrylic acid methyl ester (GEM 92)

A solution of 3-(3'-adamantan-1-yl-4'-carboxymethoxybi-phenyl-4-yl)acrylic acid methyl ester (Example 9, Step 2) (257 mg, 0.576 mmol), WSC (169 mg, 0.864 mmol), N-hydroxysuccinimide (102 mg, 0.864 mmol) in anhydrous DMF (5.58 mol) was stirred at room temperature 3h and during this time a white insoluble solid formed. This suspension was transferred, under nitrogen, into a flask containing $NH_2NH_2 \cdot H_2O$ (59 mg, 1.15 mmol), cyclohexene (15 L) and $CH_3CN$ (3 mL) at 0° C. The resulting mixture was stirred at room temperature overnight then solvents were evaporated and the white residue washed with water. Purification by flash chromatography ($CH_2Cl_2$/MeOH 196:4) gave 223 mg (84%) of the product as white solid, m.p. 195° C., $R_f$ ($CH_2Cl_2$/MeOH 196:4 0.21. $^1$H-NMR (300 MHz, DMSO-$d_6$) δ: 9.17 (1H, s); 7.79-7.61 (5H, m); 7.50 (1H, dd, J=8.49, 2.06 Hz); 7.43 (1H, d, J=2.06 Hz); 6.96 (1H, d, J=8.49 Hz); 6.64 (1H, d, J=16.2 Hz); 4.52 (2H, s); 4.36 (2H, d, J=3.62 Hz); 3.71 (3H, s); 2.20-1.96 (9H, m); 1.82-1.63 (6H, m).

Step 2: 3-(3'-adamantan-1-yl-4'-hydrazinocarbonyl-methoxy-biphenyl-4-yl)-acrylic acid trifluoroacetate (17, GEM 93)

Into an ice-cooled solution of the above methyl ester (GEM 92) (106 mg, 0.211 mmol) in 6.65 ml of $CH_2Cl_2$ was dropped TFA (2.11 ml). The mixture was left 2 h at 0° C. under nitrogen. Evaporation of the solvent gave 116 mg (98%) of product as white solid, m.p.>290° C., $^1$H-NMR (300 MHz, DMSO-$d_6$) δ: 7.76-7.63 (4H, m); 7.60 (1H, d, J=16.1 Hz); 7.51 (1H, dd, J=8.43, 1.34 Hz); 7.44 (1H, d, J=1.34 Hz); 6.96 (1H, d, J=8.43 Hz); 6.53 (1H, d, J=16.1 Hz); 4.72 (2H, s); 2.21-1.97 (9H, m); 1.83-1.63 (6H, m).

Example 18

3-(4'-Hydroxycarbamoylmethoxy-biphenyl-4-yl)-acrylic acid (18) (GEM 103)

Step 1: 3-(4'-Ethoxycarbonylmethoxy-biphenyl-4-yl)-acrylic acid tert-butyl ester (GEM 96)

A solution of 3-(4'-Hydroxy-biphenyl-4-yl)-acrylic acid tert-butyl ester (Giannini, G. et al. Bioorganic & Medicinal Chemistry (2012), 20(7), 2405-2415) (500 mg, 1.69 mmol) and of ethyl bromoacetate (582 mg, 3.38 mmol) in 10 ml of DMF was added with $K_2CO_3$ (934 mg, 6.76 mmol) and heated 2 h at 80° C. DMF was evaporated and the residue was poured into water. After being stirred for 15' the white solid formed was filtered and dried. Crystallization from ethyl ether gave 475 mg (74%) of the desired compound as a white solid, m.p. 137° C., $R_f$(Hexane/Ethyl acetate 90:10) 0.19.

$^1$H-NMR (300 MHz, CDCl$_3$) δ: 7.63 (1H, d, J=16.3 Hz); 7.60-7.53 (6H, m); 7.01 (2H, d, J=8.63 Hz); 6.41 (1H, d, J=16.3 Hz); 4.68 (2H, s); 4.31 (2H, q, J=7.29 Hz); 1.57 (9H, s); 1.33 (3H, t, J=7.29 Hz).

Step 2: 3-(4'-Carboxymethoxy-biphenyl-4-yl)-acrylic acid tert-butyl ester (GEM 99)

To a solution of the above ester (440 mg, 1.15 mmol) in 35.6 ml of aq. 50% THF was added LiOH·H$_2$O (241 mg, 5.75 mmol) and the mixture was stirred at rt overnight. After evaporation of THF, KHSO$_4$ 1M (45 ml) was added and the white solid precipitated was filtered. Crystallization from diethyl ether gave 357 mg (88%) of the desired compound as white solid, m.p.>290° C., $R_f$($CH_2Cl_2$/MeOH 18:2) 0.15. $^1$H-NMR (300 MHz, DMSO) δ: 12.9 (1H, brs); 7.79-7.63 (6H, m); 7.58 (1H, d, J=16.3 Hz); 7.01 (2H, d, J=8.78 Hz); 6.54 (1H, d, J=16.3 Hz); 4.73 (2H, s); 1.50 (9H, s).

Step 3: 3-{4'-[Tetrahydro-pyran-2-yloxycarbamoyl)-methoxy]-biphenyl-4-yl}-acrylic acid tert-butyl ester (GEM 100)

Into an ice-cooled suspension of the above ester (200 mg, 0.564 mmol) in 5.73 ml of dry DMF, under nitrogen, HBTU (214 mg, 0.564 mmol) and DIPEA (218 mg, 1.69 mmol) were added. After two minutes 69 mg (0.564 mmol) of O-(tetrahydro-pyran-2-yl)-hydroxylamine were added and the mixture was left overnight at rt. DMF was evaporated, the residue was taken up with 5 ml of water and stirred at rt for 15 minutes. Then the white solid was filtered and purified by flash chromatography on silica gel (hexane/EtOAc 55:45) to give 161 mg (52%) of product as white solid, m.p. 148° C., $R_f$ (hexane/ethyl acetate 70:30) 0.24. $^1$H-NMR (300 MHz, CDCl$_3$) δ: 9.12 (1H, s); 7.61 (1H, d, J=16.3 Hz); 7.57-7.53 (6H, m); 7.00 (2H, d, J=8.41 Hz); 6.39 (1H, d, J=16.3 Hz); 5.05-5.00 (1H, m); 4.63 (2H, s); 4.06-3.95 (1H, m); 3.70-3.61 (1H, m); 1.92-1.78 (3H, m); 1.66-1.56 (3H, m); 1.54 (9H, s).

Step 4: 3-(4'-Hydroxycarbamoylmethoxy-biphenyl-4-yl)-acrylic acid (18, GEM 103)

Into an ice-cooled solution of 3-{4'-[Tetrahydro-pyran-2-yloxycarbamoyl)-methoxy]-biphenyl-4-yl}-acrylic acid tert-butyl ester (127 mg, 0.280 mmol) in 2.62 ml of $CH_2Cl_2$ was dropped TFA (0.874 ml). The mixture was left 2 h at 0° C. under nitrogen and during this time a pink solid formed. The solid was filtered, washed with cold $CH_2Cl_2$ and dried to give 85 mg (97%) of product as white solid, m.p. 239° C., $^1$H-NMR (300 MHz, DMSO-$d_6$) δ: 12.3 (1H, br s); 10.8 (1H, s); 8.95 (1H, br s); 7.79-7.66 (6H, m); 7.62 (1H, d, J=16.3 Hz); 7.06 (2H, d, J=8.88 Hz); 6.55 (1H, d, J=16.3 Hz); 4.52 (2H, s).

Examples 19-23

Evaluation of Biological Activity
Cell Lines
Human NCI-H460 NSCLC, H460-R9A (Adarotene-resistant NCI-H460) NSCLC, A2780 and A2780-Dx (multidrug resistant) ovarian carcinoma, MDA-MB436 breast carcinoma, MM288, MM317, MM404, MM473, and MM481 epithelioid mesothelioma, MM487 and MM491 biphasic mesothelioma, MM432 and MM472 sarcomatoid mesothelioma, MM487Luc (luciferase-expressing) biphasic mesothelioma, U87MG-Luc glioma, U937 histiocytic lymphoma, RAJI, DG-75, and RAMOS Burkitt lymphoma, JECO-1, MAVER-2, MINO, REC-1, and Z-138 mantle cell lymphoma, KM-H2 and L-428 Hodgkin lymphoma, OCI-LY3 and U-2932 diffuse large B-cell lymphoma, NB4 promyelocytic leukemia (APL).

Cell Cultures

NCI-H460, H460-R9A, A2780, A2780-Dx, NB4, U937, RAJI, REC-1, DG-75, U-2932, KM-H2, L-428 cells were cultured in RPMI-1640 medium supplemented with 10% FBS, 2 mM L-glutamine and gentamicin sulphate. MDA-MB436 cells were cultured in DMEM medium supplemented with 10% FBS, 2 mM L-glutamine and gentamicin sulfate. MM288, MM317, MM404, MM473, MM481, MM487, MM491, MM432, MM472 cells were cultured in Ham's F-10 Nutrient Mixture supplemented with 10% FBS, 2 mM L-glutamine, and gentamicin sulphate, MM487Luc cells were cultured in Ham's F-10 Nutrient Mixture supplemented with 10% FBS, 2 mM L-glutamine, and G418 antibiotic. U87MG-Luc cells were cultured in EMEM medium supplemented with 10% FBS, 2 mM L-glutamine and gentamicin sulfate. RAMOS, OCI-LY3, JECO-1, MAVER-2, MINO cells were cultured in RPMI-1640 medium supplemented with 20% FBS, 2 mM L-glutamine and gentamicin sulfate. Z-138 cells were cultured in IMDM medium supplemented with 10% FBS, L-glutamine and gentamicin sulfate.

Cells were maintained in a 37° C. incubator with saturated humidity and an atmosphere of 95% air and 5% CO2, and were sub-cultured every 2-3 days.

Experimental Design

The anti-proliferative activity of a number of new atypical retinoids (AR) was assessed on various human cell lines from solid and hematological cancers.

To this end, cells in logarithmic phase of growth were seeded in 96-wells plastic plates, incubated overnight in culture medium, and treated with scalar concentrations of the compounds for either 24 h followed by 48 h recovery in drug-free-medium, or 72 h. Cell survival was finally assayed by the SRB (sulphate reducing bacterial) or MTT test and the IC50 value (drug concentration inhibiting 50% of cell growth) calculated by the ALLFIT program.

Results

The following Tables 1-7 report examples of anti-proliferative activity of selected compounds.

Example 19

Tumor cells were exposed for 24 h to new atypical retinoids (AR) and the anti-proliferative activity assessed upon 48 h recovery in drug-free medium with the SRB assay. Results are reported in the following table 1.

TABLE 1

| Human NCI-H460 NSCLC exposed to new atypical retinoids | |
|---|---|
| Compound | IC$_{50}$ ± SD (µM) |
| 8 (MIR002) | ≤0.5 |

Example 20

Tumor cells were chronically treated with various atypical retinoids and the anti-proliferative activity assessed upon 72 h with the SRB assay. Results are reported in the following table 2.

TABLE 2

| Human NCI-H460 NSCLC chronically exposed to new atypical retinoids | |
|---|---|
| Compound | IC$_{50}$ ± SD (µM) |
| 1 (RC1315) | <5 |
| 2 (RC1375) | <5 |
| 3 (RC1268) | ≤5 |
| 4 (RC1363) | ≤10 |
| 5 (RC1338) | <5 |
| 6 (AB514) | <0.1 |
| 8 (MIR002) | <0.5 |

Example 21

Tumor cells were exposed for 24 h to new atypical retinoids (AR) and the anti-proliferative activity assessed upon 48 h recovery in drug-free medium with the SRB assay. RI=Resistance Index (ratio between the IC50 values of resistant and sensitive cells). Results are reported in the following table 3.

TABLE 3

| Human Adarotene-resistant NCI-H460 (R9A) NSCLC, MM487-Luc mesothelioma, parent A2780 and A2780-Dx multidrug-resistant ovarian cancer cell lines, U87MG glioblastoma cells exposed to new atypical retinoids. | | | | | | |
|---|---|---|---|---|---|---|
| | IC$_{50}$ ± SD (µM) | | | | | |
| Compound | H460-R9A | MM487-Luc | U87MG | A2780 | A2780-Dx | RI |
| Adarotene (ST1926) | 26.9 ± 0.7 | 9.2 ± 0.3 | 1.63 ± 0.1 | | | |
| 1 (RC1315) | 8.3 ± 0.2 | 1.7 ± 0.08 | | 4.2 ± 0.3 | 3.9 ± 0.1 | 0.9 |
| 2 (RC1375) | 5.9 ± 0.1 | 1.9 ± 0.2 | 5.5 ± 0.9* | 3.7 ± 0.3 | 4.5 ± 0.07 | 1.3 |
| 8 (MIR002) | 2.8 ± 0.3 | 4.5 ± 0.3 | 1.1 ± 0.3 | 0.6 ± 0.01 | 0.41 ± 0.005 | 0.7 |
| 12 (GEM 60) | 10.6 ± 0.3 | | | | | |
| 13 (GRM 59) | 16.9 ± 0.5 | | | | | |
| 14 (GEM 61) | 2.3 ± 0.4 | | | | | |
| 17 (GEM 93) | 17.3 ± 1.3 | | | | | |

As described by Zuco V. et al in Neoplasia, 2005 July; 7(7):667-77, H460-R9A are about 70 fold resistant with respect to parental H460 to Adarotene. Surprisingly, the new retinoid derivatives showed a significantly increase of cytotoxic activity against this cell line compared to Adarotene. Ovarian cancer A2780 and its clone derivative A2780DX (Doxorubicin resistant) which overexpress P-glycoprotein (PGP), were used to evaluate the possibility of these new molecules to be absorbed at intestinal level. In fact, the overexpression of PGP, as well known, drastically reduces the possibility, after oral administration, of absorption of several chemotherapeutic agents (i.e. Paclitaxel, doxorubicin etc.). Since the IC50 of the tested compounds in A2780 and A2780DX, have similar values we conclude that they are not PGP substrates and they could be administrated to the patients via oral route. Moreover, the antitumor activity of 2 and 8 on Glioblastoma tumor cells (U87MG) suggest the use of this class of compounds in intracranial tumors including Glioma.

Example 22

Tumor cells were exposed for 24 h to new atypical retinoids (AR) and the anti-proliferative activity assessed upon 48 h recovery in drug-free medium with the MTT assay.

Results are reported in the following table 4.

TABLE 4

Human hematological cancer cell lines exposed to new atypical retinoids.

| Cell lines | IC50 ± SD (μM) 8 (MIR002) |
|---|---|
| Z-138 mantle cell lymphoma | 0.074 ± 0.02 |
| NB4 (pro-myelocytic. leukemia) | 0.18 ± 0.04 |

Example 23

Evaluation of Antitumor Activity of Compounds 2 (RC1375) and 8 (MIR002) on Xenograft Mouse Model
Materials and Methods
Animals CD-1 nude and NOG mice, females, 4-5 weeks-old, were housed under specific-pathogen-free conditions in individually ventilated cages. Ethics approval was obtained from the Italian Ministry of Health and all experiments were in accordance with the European guidelines for the care and use of laboratory animals.
Cell Cultures and Tumor Implants Cells were cultured in appropriated media and expanded in a 37° C. incubator with saturated humidity and an atmosphere of 95% air and 5% $CO_2$, and were sub-cultured every 2-3 days. Before the injection in mice, cells were checked with MycoAlert® Mycoplasma Detection Kit (Lonza) to exclude mycoplasma contamination, counted by trypan blue dye exclusion, evaluated for cell viability (>95%).

H-460-R9A lung cancer cells were suspended at a concentration of $25 \times 10^6$/ml. $5 \times 10^6$ tumor cells were suspended in 0.2 ml of M199, then inoculated subcutaneously on the right flank of each animal.
Orthotopic Mesothelioma Model (MM473-Luc) were re-suspended at the concentration of $1 \times 10^6$ cells/40 μl M199 medium., then orthotopically injected intrapeulically with infusion of 1/min (with Hamilton syringe).

Orthotopic glioma murine model. $1 \times 10^6$ Brain glioblastoma bioluminescent cells (U-87 MG) were injected intracranically and tumor growth was evaluated through IVIS imaging system.
Reagents and In Vivo Treatments Different concentrations of compound 2 (RC1375) were diluted in 10% 1:1 absolute Ethanol-Cremophor solution in saline. Compound and vehicle were administered IP at the volume of 5 ml/kg. MIR002 was dissolved to a concentration of 3.3 mg/mL in 10% DMSO, 5% ethanol, 20% Kolliphor® EL and 65% $Na_2CO_3$ 10 mM pH 11 and administered by gavage; Cisplatin was dissolved to a concentration of 0.8 mg/mL in sterile saline solution and administered intravenously.
Measurements and In Vivo Imaging Four days after inoculation, tumor masses of H460-R9A were measured in length and width using a Mitutoyo caliper, mice were sorted basing on tumor volume (TV) and treatments were started. Tumor volume was calculated as follows: TV (mm3)=(Length (mm)×Width (mm)2)/2. Tumor growth was followed by biweekly measurements. Tumor Growth Inhibition (TGI) for each group was calculated as follows: TGI (%)=100−(mean TVtreated/mean TVcontrol× 100). Mice were weighed twice a week. In-vivo tumor engraftment of luciferase expressing tumors was followed by biweekly radiance (BLI) measurements using IVIS Spectrum (Perkin Elmer), 30 minutes after intraperitoneal administration of 15 mg/kg D-Luciferine. 12 days after cells inoculation, animals were sorted basing on BLI and treatments were started. Tumor growth was further followed by weekly BLI measurements. TGI was calculated as for the H460 trial.
Statistical Analysis Statistical analysis was performed by using U-Test (GraphPad Prism 6). Outliers were removed by using the Rout test (Q=10%, GraphPad Prism 6).
Results The activity of compound 2 (RC1375) was evaluated on glioma xenograft murine models. Brain glioblastoma bioluminescent cells (U-87 MG) were injected intracranically and tumor growth was evaluated through IVIS imaging system. After a week of injection, 2 (RC1375) (100 mg/kg) was administered intraperitoneally to mice (qdx5x4w). As shown in FIG. 1, treatment with compound 2 (RC1375) determines a significant tumor reduction with a TGI of 72%.

All the results are summarized in the table 5 below.

TABLE 5

| Tumor cell line | No of mice | Treatment | Route and dose | Tumor growth (day) BLI (p/s/cm²/sr) Average (Day) | Tumor volume (mm³) | TGI (%) |
|---|---|---|---|---|---|---|
| U87MG-Luc (Glioma) | 5 | 2 (RC1375) | 100 mg/kg – IP | $1.31 \times 10^5 \pm 1.26 \times 10^5$ (+35) | | 72 |
| | 5 | Vehicle | –IP | $4.78 \times 10^5 \pm 2.85 \times 10^5$ (+35) | | — |

BW = body weight, TGI = tumor growth inhibition, BLI = units of Bioluminescent imaging.

The antitumor activity of compound MIR002 (8) was evaluated in Mesothelioma tumor model MM473 and NSCLC H460. In both models the compound was administered orally using the schedule and doses reported in tables 6 and 7. In both models MIR002 significantly reduced tumor growth evaluated as TGI.

Interestingly, the combination of MIR002 with cisplatin in resistant H460-R9A cell line significantly reduced the tumor growth with respect to the drugs administered alone.

TABLE 6

MIR002 (8) significantly reduced tumor growth of human Pleural Epithelioid Mesothelioma MM473 orthotopically xenografted on nude mice

| Administered Compound | Route of Administration | Dose/ Volume | Schedule | BWL Day + 35 (%) | TGI Day + 35 (%) |
|---|---|---|---|---|---|
| Vehicle | OS | — | bid, qdx5/ wx3w | 0 | — |
| MIR002 (8) | OS | 50 mg/kg | bid, qdx5/ wx4w | 0 | 77 |

TABLE 7

Compound 8 (MIR002) exerted a strong in-vivo antitumor activity on H460-R9A retinoid resistant cells, which was comparable to and synergistic with the activity of Cisplatin, without affecting body weight. On the contrary, Adarotene (ST1926) resulted not active although administered at its pharmacological active dose.

| Administered Compound(s) | Route of Administration | Dose | Schedule | BWL Day + 35 (%) | TGI Day + 35 (%) |
|---|---|---|---|---|---|
| Vehicle | OS + IV | — | bid, qdx5/wx4w q7dx4w | 0 | — |
| Adarotene (ST1926) | OS | 15 mg/Kg | q7dx5x4w | 12 | — |
| Cisplatin | IV | 4 mg/kg | q7dx4w | 2, 4 | 34 |
| MIR002 (8) | OS | 50 mg/kg | bid, qdx5/wx4w | 0 | 38 |
| MIR002 (8) + Cisplatin | OS + IV | 50 mg/kg 4 mg/kg | bid, qdx5/wx4w q7dx4w | 0 | 78 |

Taken together, the results from in vitro and in vivo experiments indicate that this new class of synthetic retinoids, including compounds 2 (RC1375), and 8 (MIR002), possesses a very large spectrum of anti-tumoral activity against several tumor histotypes suggesting their therapeutic use for the treatment of different human cancers.

Moreover, the administration of these compounds alone or in combination with Cisplatin did not show any negative effect on mice body weight, thus suggesting an high tolerability.

Example 24

Synthesis of MIR002, GEM144, BIO146

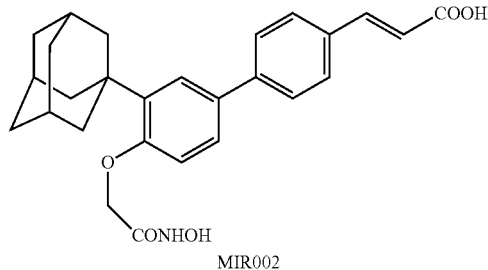
MIR002

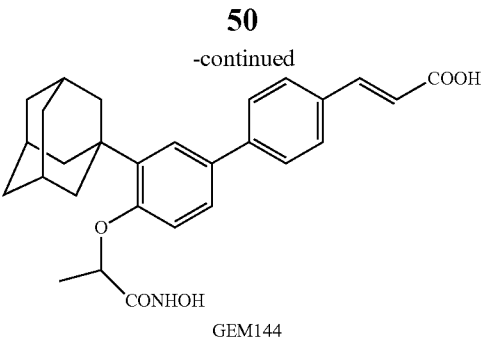
GEM144

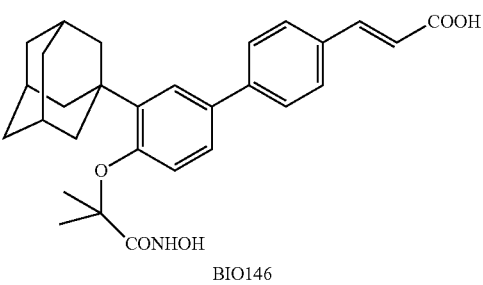
BIO146

Synthesis (E)-3-(3'-adamantan-1-yl)-4'-(2-(hydroxyamino)-2-oxoethoxy)-[1,1'-biphenyl]-4-yl) acrylic acid (MIR002)

A) 3-(3'-Adamantan-1-yl-4'-ethoxycarbonyl-methoxy-biphenyl-4-yl)-acrylic acid tert-butyl ester A mixture of 3-(3'-adamantan-1-yl-4'-hydroxy-biphenyl-4-yl)-acrylic acid tert-butyl ester (2.00 g, 4.64 mmol), ethyl bromoacetate (1.58 g, 9.28 mmol), K2CO3 (2.57 g, 18.6 mmol) in 40 ml of DMF was heated at 80° C. for 1 h. $K_2CO_3$ was filtered, DMF evaporated and the residue was taken up with water. The solid precipitated was filtered and crystallized from diethyl ether to give 2.09 g (97%) of the title compound as a white solid, m.p. 175° C., Rf (petroleum ether/ethyl acetate 90:10) 0.31. 1H-NMR (300 MHz, CDCl$_3$) δ: 7.61 (1H, d, J=15.9 Hz), 7.58-7.53 (4H, m), 7.50 (1H, d, J=2.35 Hz), 7.39 (1H, dd, J=8.39 Hz, J=2.35 Hz), 6.79 (1H, d, J=8.39 Hz), 6.38 (1H, d, J=15.9 Hz), 4.67 (2H, s), 4.31 (2H, q, J=7.16 Hz), 2.23-2.07 (9H, m), 1.88-1.74 (6H, m), 1.54 (9H, s), 1.32 (3H, t, J=7.16 Hz). 13C-NMR (75 MHz, CDCl$_3$) δ: 168.7, 166.4, 156.7, 143.2, 142.9, 139.2, 133.2, 132.9, 128.4 (×2C), 127.1 (×2C), 126.0, 125.2, 119.6, 112.2, 80.4, 65.4, 61.3, 40.5 (×3C), 37.2, 37.0 (×3C), 29.1 (×3C), 28.2 (×3C), 14.2.

B) 3-(3'-Adamantan-1-yl-4'-carboxymethoxy-biphenyl-4-yl)-acrylic acid tert-butyl ester To a solution of 3-(3'-Adamantan-1-yl-4'-ethoxycarbonylmethoxy-biphenyl-4-yl)-acrylic acid tert-butyl ester (2.08 g, 4.02 mmol) in 125 ml of aq. 50% THF was added with 843 mg (20.1 mmol) of LiOH·H2O and left overnight at rt. Evaporation, taking up with EtOAc, washing with 60 ml of 1N KHSO4, extraction with EtOAc, drying the extracts with Na₂SO₄, filtration and evaporation gave 1.92 g (98%) of the product, white solid, m.p.>300° C., Rf (CH₂Cl₂/MeOH 19:1) 0.23. 1H-NMR (300 MHz, DMSO-d6) δ: 7.75-7.60 (4H, m), 7.56 (1H, d, J=15.8 Hz), 7.48 (1H, dd, J=8.51 Hz, J=2.36 Hz), 7.43 (1H, d, J=2.36 Hz), 6.93 (1H, d, J=8.51 Hz), 6.51 (1H, d, J=15.8 Hz), 4.70 (2H, s), 2.19-1.98 (9H, m), 1.83-1.66 (6H, m), 1.48 (9H, s). 13C-NMR (75 MHz, DMSO-d6) δ: 170.4, 166.1, 157.2, 143.7, 142.5, 138.6, 132.9, 132.1, 129.3 (×2C), 127.0 (×2C), 125.5, 125.2, 119.7, 113.5, 80.3, 65.3, some signals are missing due to the overlap with solvent, 37.1, 37.9, 28.9 (×3C), 28.3 (×3C).

C) 3-{3'-Adamanan-1-yl-4'-[(tetrahydropyran-2-yloxycarbamoyl)-methoxy]-biphenyl-4-yl}-acrylic acid tert-butyl ester Into an ice-cooled suspension of 3-(3'-Adamantan-1-yl-4'-carboxymethoxy-biphenyl-4-yl)-acrylic acid tert-butyl ester (1.25 g, 2.56 mmol) in 26 ml of dry DMF, under nitrogen, HBTU (0.971 g, 2.56 mmol) and DIPEA (0.993 g, 7.68 mmol) were added. After two minutes 0.312 g (2.56 mmol) of O-(tetrahydro-pyran-2-yl)-hydroxylamine were added and the mixture was left overnight at rt. DMF was evaporated, the residue was taken up with water and the white solid filtered. Purification by flash chromatography on silica gel with petroleum ether/EtOAc 7:3 gave 1.23 g of the product, white solid, m.p. 193° C., Rf (AcOEt/petroleum ether 3:7) 0.31. 1H-NMR (300 MHz, CDCl₃) δ: 9.13 (1H, s), 7.61 (1H, d, J=16.0 Hz), 7.58-7.54 (4H, m), 7.51 (1H, d, J=2.24 Hz), 7.43 (1H, dd, J=8.53 Hz, J=2.24 Hz), 6.91 (1H, d, J=8.53 Hz), 6.39 (1H, d, J=16.0 Hz), 5.07-5.02 (1H, m), 4.68 (2H, s), 4.00-3.90 (1H, m), 3.67-3.57 (1H, m), 2.18-2.11 (9H, m), 1.92-1.78 (8H, m), 1.70-1.58 (4H, m), 1.54 (9H, s). 13C-NMR (300 MHz, CDCl₃) δ: 166.4, 165.1, 156.1, 143.1, 142.5, 138.8, 134.2, 133.2, 128.4 (×2C), 127.1 (×2C), 126.2, 125.6, 119.8, 113.4, 102.8, 80.5, 67.6, 62.5, 41.1 (×3C), 37.1, 37.0 (×3C), 28.9 (×3C), 28.2 (×3C), 27.9, 24.9, 18.5.

D) (E)-3-(3'-adamantan-1-yl)-4'-(2-(hydroxyamino)-2-oxoethoxy)-[1,1'-biphenyl]-4-yl)acrylic acid 3-{3'-Adamantan-1-yl-4'-[(tetrahydropyran-2-yloxycarbamoyl)-methoxy]-biphenyl-4-yl}-acrylic acid tert-butyl ester (250 mg, 0.425 mmol) was added portionwise to 3.5 ml of TFA at 0° C. under nitrogen and the mixture was stirred at 0° C. for 1h. The pink suspension was filtered, the solid was washed with water until neutral pH to give 175 mg (92%) of desired compound as white solid, m.p. 265° C., Rf (CH₂Cl₂/MeOH 18:2) 0.49. 1H-NMR (300 MHz, CDCl₃+TFA) δ: 7.91 (1H, d, J=16.0 Hz), 7.67-7.59 (4H, m), 7.55 (1H, d, J=2.22 Hz), 7.47 (1H, dd, J=8.30 Hz, J=2.22 Hz), 6.90 (1H, d, J=8.30 Hz), 6.49 (1H, d, J=16.0 Hz), 4.78 (2H, s), 2.20-2.10 (9H, m), 1.91-1.72 (6H, m). 13C-NMR (300 MHz, DMSO-d6) δ: 168.1, 164.8, 157.7, 144.0, 142.5, 138.8, 133.0, 132.3, 129.2 (×2C), 127.1 (×2C), 125.6, 125.2, 119.1, 114.0, 66.4, (5C missing due to the overlap with signal solvent), 37.1, 36.9, 28.9 (×3C).

Synthesis of (E)-3-(3'-adamantan-1-yl)-4'-((1-(hydroxyamino)-1-oxopropan-2-yl)oxy)-[1,1'-biphenyl]-4-yl)acrylic acid (GEM144)

(E)-3-(3'-adamantan-1-yl)-4'-((1-ethoxy-1-oxopropan-2-yl)oxy)-[1,1'-biphenyl]-4-yl)acrylic acid tert-butyl ester To a solution of 3-(3'-adamantan-1-yl-4'-hydroxy-biphenyl-4-yl)-acrylic acid tert-butyl ester (500 mg, 1.16 mmol) in dry acetone (7 mL), K₂CO₃ (641 mg, 4.64 mmol), KI (13 mg, 0.08 mmol) and 2-bromopropionic acid ethyl ester (180 μL, 1.39 mmol), were added under nitrogen. The mixture was heated 5 h to reflux. K₂CO₃ was filtered, and the solvent removed in vacuo. The crude was triturated with hexane:diethyl ether 5:1, the precipitate was filtered to give 340 mg of title compound. Yield: 55%. m.p. 88° C., Rf (petroleum ether/ethyl acetate 92.5:7.5) 0.30.

1H-NMR (300 MHz, CDCl3) δ: 7.61 (1H, d, J=15.7 Hz), 7.57-7.52 (4H, m), 7.49 (1H, d, J=2.3 Hz), 7.35 (1H, dd, J=2.3, 8.4 Hz), 6.71 (1H, d, J=8.4 Hz), 6.38 (1H, d, J=15.7 Hz), 4.88 (1H, q, J=6.6 Hz), 4.22 (2H, q, J=7.1 Hz), 2.31-2.14 (6H, m), 2.13-2.04 (3H, m), 1.84-1.74 (6H, m), 1.71 (3H, d, J=6.6 Hz), 1.54 (9H, s), 1.25 (3H, t, J=7.1 Hz).

(E)-3-(3'-adamantan-1-yl)-4'-(1-carboxyethoxy)-[1,1'-biphenyl]-4-yl)acrylic acid tert-butyl ester To a solution of (E)-3-(3'-adamantan-1-yl)-4'-((1-ethoxy-1-oxopropan-2-yl)oxy)-[1,1'-biphenyl]-4-yl)acrylic acid tert-butyl ester (500 mg, 0.94 mmol) in aq. 50% THF (30 mL), LiOH·H₂O (198 mg, 4.71 mmol) was added. The solution was stirred overnight at rt. The solvent was evaporated, the crude was diluted in 1N KHSO₄ and extracted with EtOAc. The combined organic extracts were washed with brine, dried over anhydrous Na₂SO₄ and concentrated in vacuo, to give 462 mg (98%) of title compound (white solid), m.p. 206° C., Rf (CH2Cl2/MeOH 193:7) 0.23. 1H-NMR (300 MHz, DMSO-d6) δ: 7.76-7.60 (m, 4H), 7.56 (d, 1H, J=15.9 Hz), 7.47 (dd, 1H, J=2.0, 8.4 Hz), 7.43 (d, 1H, J=2.0 Hz), 6.80 (d, 1H, J=8.4 Hz), 6.51 (d, 1H, J=15.9 Hz), 4.91 (q, 1H, J=6.5 Hz), 2.24-2.00 (m, 9H), 1.79-1.66 (m, 6H), 1.57 (d, 3H, J=6.5 Hz), 1.47 (9H, s).

(E)-3-(3'-adamantan-1-yl)-4'-((1-oxo-1-(((tetrahydro-2H-pyran-2-yl)oxy)amino)propan-2-yl)oxy)-[1,1'-biphenyl]-4-yl)acrylic acid tert-butyl ester To a solution of (E)-3-(3'-adamantan-1-yl)-4'-(1-carboxyethoxy)-[1,1'-biphenyl]-4-yl)acrylic acid tert-butyl ester (400 mg, 0.79 mmol) in dry DMF (6 mL), HBTU (302 mg, 0.79 mmol) and DIPEA (423 μL, 2.38 mmol) were added at 0° C. under nitrogen atmosphere. The solution was stirred 30 min at 0° C. then O-(tetrahydropyran-2-yl)-hydroxylamine (93 mg, 079 mmol) was added and the reaction was stirred overnight at rt. The solvent was removed in vacuo, the residue was triturated with water and filtered. The crude was purified by flash column chromatography in hexane:ethyl acetate 3:1 to give 400 mg of title compound. Yield: 84%, Rf (hexane:ethyl acetate 7:3) 0.32. 1H-NMR (300 MHz, CDCl₃) δ: mixture of stereoisomer 8.98 (1H, s), 8.87 (1H, s), 7.61 (2H, d, J=15.8 Hz), 7.57-7.53 (8H, m), 7.51 (2H, d, J=2.3 Hz), 7.45-7.35 (2H, m), 6.91-6.83 (2H, m), 6.38 (2H, d, J=15.9 Hz), 5.03-4.81 (4H, m), 3.90-3.76 (2H, m), 3.64-3.54 (1H, m), 3.50-3.38 (1H, m), 2.26-2.07 (18H, m), 1.84-1.76 (12H, m), 1.69-1.74 (6H, m), 1.54 (18H, s).

(E)-3-(3'-adamantan-1-yl)-4'-((1-(hydroxyamino)-1-oxopropan-2-yl)oxy)-[1,1'-biphenyl]-4-yl)acrylic acid To a solution of (E)-3-(3'-adamantan-1-yl)-4'-((1-oxo-1-(((tetrahydro-2H-pyran-2-yl)oxy)amino)propan-2-yl)oxy)-[1,1'-biphenyl]-4-yl)acrylic acid tert-butyl ester (1.35 g, 2.20 mmol) in dry CH2Cl2 (22 mL) at 0° C., TFA (22 mL) was dropwise under nitrogen. The solution was stirred at 0° C. for 4h. The mixture was evaporated and treated with toluene to remove TFA, the solid obtained was triturated in $CH_2Cl_2$ and filtrated to give 646 mg of title compound. Yield: 64%., Rf ($CH_2Cl_2$/MeOH/$H_2O$ 18:2:0.2) 0.35. 1H-NMR (300 MHz, CDCl3+TFA) δ: 7.92 (1H, d, J=15.9 Hz), 7.68-7.59 (4H, m), 7.57 (1H, d, J=2.2 Hz), 7.44 (1H, dd, J=2.2 Hz, 8.3 Hz), 6.80 (1H, d, J=8.3 Hz), 6.49 (1H, d, J=15.9 Hz), 5.10-4.95 (1H, m), 2.28-2.03 (9H, m), 1.91-1.68 (9H, m).

(E)-3-(3'-adamantan-1-yl)-4'-((1-(hydroxyamino)-2-methyl-1-oxopropan-2-yl)oxy)-[1,1'-biphenyl]-4-yl) acrylic acid (BIO 146)

2-(2-Adamantan-1-yl-4-bromophenoxy)-2-methyl-propionic acid

To a solution of 2-adamantan-1-yl-4-bromophenol (100 mg, 0.32 mmol) in methyl ethyl ketone (1 mL), NaOH (65 mg, 1.62 mmol, 5 equiv) was added. The mixture was heated to 50° C. and stirred at 50° C. for 2 h. A solution of α-bromoisobutyric acid (98 mg, 0.58 mmol, 1.8 equiv) in methyl ethyl ketone (0.3 mL) was added to the suspension. The reaction mixture was stirred at 50° C. for an additional 3 h. The solvent was removed in vacuo, the crude was triturated with diethyl ether and the resulting solid was filtered. Then it was suspended in 1N HCl, washed with water and filtered to give 123 mg of title compound. The compound was used in the next step without further purification.

2-(2-adamantan-1-yl-4-bromo-phenoxy)-2-methyl-N-(tetrahydropyran-2-yloxy) propionamide To a solution of 2-(2-adamantan-1-yl-4-bromophenoxy)-2-methylpropionic acid (80 mg, 0.20 mmol) in dry DMF (1.5 ml mL), HBTU (77 mg, 0.20 mmol) and DIPEA (108 µL, 0.61 mmol) were added at 0° C. under nitrogen atmosphere. The solution was stirred 30 min at 0° C. then O-(tetrahydro-pyran-2-yl)-hydroxylamine (24 mg, 0.20 mmol) was added and the reaction was stirred overnight at rt. The solvent was removed in vacuo, the crude was diluted with water and extracted with EtOAc. The combined organic extracts were washed with brine, dried over anhydrous $Na_2SO_4$ and concentrated in vacuo. The crude was purified by flash column chromatography in petroleum ether:ethyl acetate 3:1 to give 77 mg of title compound. Yield: 77%, 1H-NMR (600 MHz, CDCl$_3$) δ: 8.86 (1H, s), 7.34 (1H, d, J=2.2 Hz), 7.20 (1H, dd, J=2.2 Hz, 8.6 Hz), 6.61 (1H, d, J=8.6 Hz), 4.98-4.94 (1H, m), 3.95-3.89 (1H, m), 3.57-3.53 (1H, m), 2.13-2.04 (9H, m), 1.87-1.73 (10H, m), 1.70-1.50 (2H, m), 1.71 (3H, s), 1.63 (3H, s).

3-{3'-Adamantan-1-yl-4'-[1-methyl-1-(tetrahydro-pyran-2-yloxycarbamoyl)-ethoxy]-biphenyl-4-yl}-acrylic acid methyl ester To a solution of 2-(2-adamantan-1-yl-4-bromo-phenoxy)-2-methyl-N-(tetrahydropyran-2-yloxy) propionamide (50 mg, 0.10 mmol) in dimethoxyethane:water 3.5:1 (2 ml, carefully degassed under nitrogen before the use), 3-[4-(4,4,5,5-tetramethyl-[1,3,2]dioxaborolan-2-yl)-phenyl]-acrylic acid methyl ester (38 mg, 0.13 mmol), PdCl2(dppf)·$CH_2Cl_2$ (4 mg, 0.005 mmol) and sodium bicarbonate (25 mg, 0.30 mmol) were added under nitrogen atmosphere. The reaction was heated at 80° C. for 4 h. Then the mixture was poured into water and extracted with ethyl acetate. The combined organic layers were dried over anhydrous Na2SO4, filtered and evaporated. Purification by flash chromatography (petroleum ether/ethyl acetate 80:20) gave 41 mg (71%) of the title compound as a white solid, Rf (hexane/ethyl acetate 80:20) 0.13. 1H-NMR (600 MHz, CDCl$_3$): 8.93 (1H, s), 7.73 (1H, d, J=15.9 Hz), 7.53-7.59 (4H, m), 7.50 (1H, d, J=2.0 Hz), 7.35 (1H, dd, J=8.4 Hz, J=2.0 Hz), 6.82 (1H, d, J=8.4 Hz), 6.46 (1H, d, J=15.9 Hz), 5.07-4.98 (1H, m), 3.95-3.87 (1H, m), 3.82 (3H, s), 3.58-3.52 (1H, m), 2.17-2.14 (6H, m), 2.14-2.08 (3H, m), 1.86-1.75 (10H, m), 1.70-1.58 (2H, m), 1.74 (3H, s), 1.70 (3H, s).

(E)-3-(3'-adamantan-1-yl)-4'-((1-(hydroxyamino)-2-methyl-1-oxopropan-2-yl)oxy)-[1,1'-biphenyl]-4-yl) acrylic acid (BIO 146)

To a solution of the above compound (34 mg, 0.06 mmol) in aq. 50% THF (2 mL), LiOH·$H_2O$ (13 mg, 0.30 mmol) was added. The solution was stirred overnight at rt. The solvent was evaporated, the crude was diluted in ice cooled 1N KHSO$_4$ and the precipitate was filtered, to give 23 mg (70%) of the acid (white solid), Rf ($CH_2Cl_2$/MeOH 95:5) 0.38.

To a solution of the above acid (23 mg, 0.04 mmol) in dry $CH_2Cl_2$ (1 mL) at 0° C., TFA (1 mL) was added dropwise under nitrogen. The solution was stirred at 0° C. for 2h. The mixture was evaporated and treated with toluene to remove TFA, the solid obtained was triturated in $CH_2Cl_2$ and filtered to give 13 mg of title compound. Yield: 68%. Rf ($CH_2Cl_2$/MeOH) 0.15. 1H-NMR (300 MHz, CDCl$_3$+TFA) δ: 7.91 (1H, d, J=16.3 Hz), 7.68-7.58 (4H, m), 7.56 (1H, d, J=2.4 Hz), 7.38 (1H, dd, J=2.4 Hz, 8.4 Hz), 6.66 (1H, d, J=8.4 Hz), 6.49 (1H, d, J=16.3 Hz), 2.21-2.08 (9H, m), 1.88-1.69 (12H, m).

Cell Lines

Human NCI-H460 and H460-R9A (atypical retinoid-resistant NCI-H460) NSCLC; A2780 and A2780-Dx (multi-drug resistant) ovarian carcinoma; MM432-Luc, MM473-Luc, and MM487Luc mesothelioma; MDA-MB231 and MDA-MB436 breast carcinoma; U87MG-Luc glioma; Z-138 mantle cell lymphoma and U-2932 diffuse large B-cell lymphoma; NB4 pro-myelocitic leukemia and THP-1 monocytic leukemia; mouse B16-Luc melanoma.

Cell Cultures

NCI-H460, H460-R9A, A2780, A2780-Dx, NB4, B16-Luc cells were cultured in RPMI-1640 medium supplemented with 10% FBS, 2 mM L-glutamine and gentamicin sulphate. MDA-MB231, MDA-MB436, Z-138, U-2932, THP-1 cells were cultured in DMEM medium supplemented with 10% FBS, 2 mM L-glutamine and gentamicin sulphate. U87MG-Luc cells were cultured in EMEM medium supplemented with 10% FBS, 2 mM L-glutamine and gentamicin sulphate. MM432-Luc, MM473-Luc, and MM487Luc cells were cultured in Ham's F-10 Nutrient Mixture supplemented with 10% FBS, 2 mM L-glutamine, 0.05 mg/mL gentamicin sulphate, and 0.4 mg/mL G418 antibiotic.

Cells were maintained in a 37° C. incubator with saturated humidity and an atmosphere of 95% air and 5% CO2, and were sub-cultured every 2-3 days.

Experimental Design

The anti-proliferative activity of the POLA1/HDAC dual inhibitors MIR002 and GEM144 was assessed on various cell lines from solid and hematological cancers. To this end, cells in the logarithmic phase of growth were seeded in 96-wells plastic plates, incubated overnight in culture medium, and treated for 72 h with scalar concentrations (2-fold dilution series) of the compounds. Cell survival was finally assayed by the SRB (solid tumors) or MTT (blood tumors) test and the IC50 value (drug concentration inhibiting 50% of cell growth) calculated by the ALLFIT program.

TABLE 8 human parent NCI-H460 and ST1926-resistant H460 (H460-R9A) NSCLC, and parent A2780 and multidrug-resistant A2780-Dx ovarian carcinoma cell lines exposed to POLA1/HDAC

| | $IC_{50} \pm SD$ (µM) | | | | | |
|---|---|---|---|---|---|---|
| Drug | NCI-H460 | H460-R9A | RI | A2780 | A2780-Dx | RI |
| MIR002 | 0.25 ± 0.006 | 2.8 ± 0.05 | 11.2 | 0.6 ± 0.01 | 0.41 ± 0.005 | 0.7 |
| GEM144 | 0.26 ± 0.009 | 2.2 ± 0.09 | 8.5 | 0.95 ± 0.04 | 0.66 ± 0.008 | 0.7 |

Human tumor cells were treated with POLA1/HDAC dual inhibitors and cell survival assessed upon 72 h with the SRB assay. HDAC=Histone Deacetylase. POLA1=DNA Polymerase Alpha 1. RI=Resistance Index.

TABLE 9

Human mesothelioma cell lines exposed to POLA1/HDAC dual inhibitors

| Drug | MM432-Luc | MM473-Luc $IC_{50} \pm SD$ (µM) | MM487-Luc |
|---|---|---|---|
| MIR002 | 1.5 ± 0.08 | 1.2 ± 0.06 | 0.22 ± 0.02 |
| GEM144 | n.e. | 1.4 ± 0.2 | 0.73 ± 0.2 |

Tumor cells were exposed to POLA1/HDAC dual inhibitors and their anti-proliferative activity assessed upon 72 h with the SRB assay. HDAC=Histone Deacetylase. POLA1=DNA Polymerase Alpha 1. N.e.=not evaluated.

TABLE 10

Solid cancer cell lines exposed to POLA1/HDAC dual inhibitors

| Drug | MDA-MB231 (Breast) | DA-MB436 (Breast) $IC_{50} \pm SD$ (µM) | 87MG-Luc (Glioma) | B16-Luc (Melanoma) |
|---|---|---|---|---|
| MIR002 | 1.9 ± 0.2 | 0.64 ± 0.03 | 1.1 ± 0.3 | 0.27 ± 0.02 |
| GEM144 | n.e. | n.e. | n.e. | 0.37 ± 0.03 |

Tumor cells were exposed to POLA1/HDAC dual inhibitors, and the anti-proliferative activity assessed upon 72 h with the SRB assay. HDAC=Histone Deacetylase. POLA1=DNA Polymerase Alpha 1. N.e.=not evaluated.

TABLE 11

Human hematological tumor cell lines exposed to POLA1/HDAC dual inhibitors

| Drug | NB4 (leukemia) | THP-1 (leukemia) $IC_{50} \pm SD$ (µM) | U2932 (lymphoma) | Z138 (lymphoma) |
|---|---|---|---|---|
| MIR002 | 0.18 ± 0.04 | 0.42 ± 0.02 | 0.52 ± 0.03 | 0.038 ± 0.003 |
| GEM144 | 0.23 ± 0.03 | 0.52 ± 0.02 | 0.77 ± 0.1 | 0.16 ± 0.03 |

Tumor cells were treated with POLA1/HDAC dual inhibitors and cell survival assessed upon 72 h with the MTT assay. HDAC=Histone Deacetylase. POLA1=DNA Polymerase Alpha 1.

Example 25

Synthesis of GEM144 and BIO 146

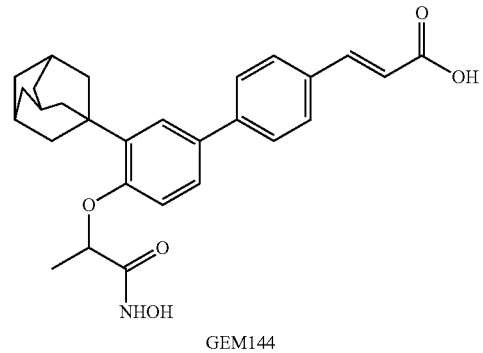

GEM144

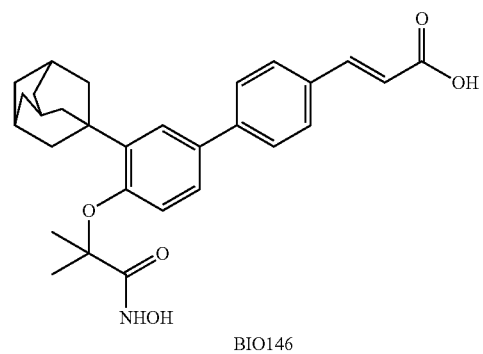

BIO146

Synthesis of GEM 144

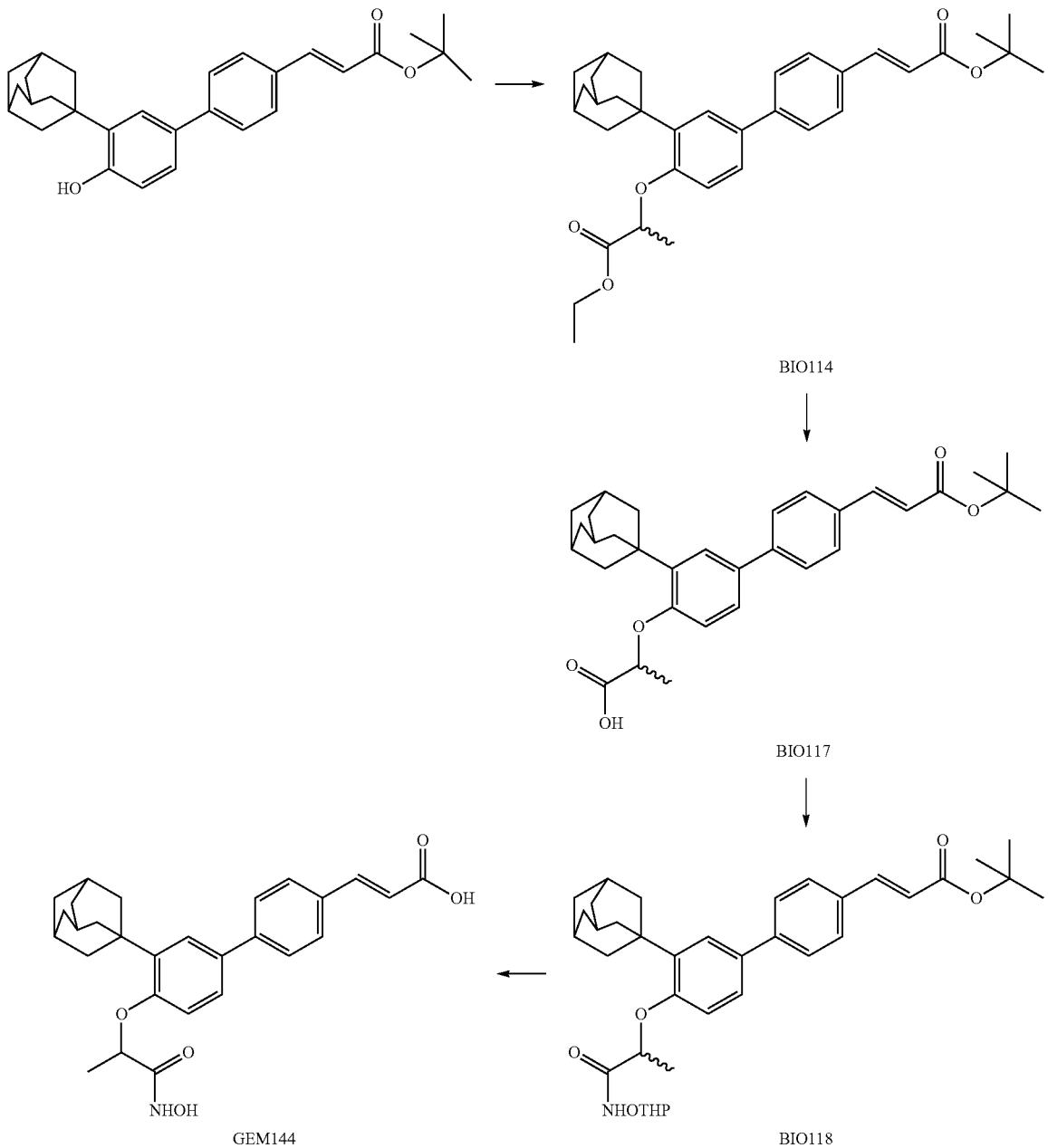

3-[3'-Adamantan-1-yl-4'-(1-ethoxycarbonylethoxy)-biphenyl-4-yl]-acrylic acid tert-butyl ester (BIO114)

To a solution of 3-(3'-adamantan-1-yl-4'-hydroxy-biphenyl-4-yl)-acrylic acid tert-butyl ester (500 mg, 1.16 mmol) in dry acetone (7 mL), K2CO3 (641 mg, 4.64 mmol), KI (13 mg, 0.08 mmol) and 2-bromo-propionic acid ethyl ester (180 μL, 1.39 mmol), were added under nitrogen. The mixture was heated 5 h to reflux. K2CO3 was filtered, and the solvent removed in vacuo. The crude was triturated with hexane:diethyl ether 5:1, the precipitate was filtered to give 340 mg of the title compound. Yield: 55%. m.p. 88° C., 1H-NMR (300 MHz, CDCl3): 7.61 (1H, d, J=15.7 Hz), 7.57-7.52 (4H, m), 7.49 (1H, d, J=2.3 Hz), 7.35 (1H, dd, J=2.3, 8.4 Hz), 6.71 (1H, d, J=8.4 Hz), 6.38 (1H, d, J=15.7 Hz), 4.88 (1H, q, J=6.6 Hz), 4.22 (2H, q, J=7.1 Hz), 2.31-2.14 (6H, m), 2.13-2.04 (3H, m), 1.84-1.74 (6H, m), 1.71 (3H, d, J=6.6 Hz), 1.54 (9H, s), 1.25 (3H, t, J=7.1 Hz).

3-[3'-Adamantan-1-yl-4'-(1-carboxy-ethoxy)-biphenyl-4-yl]-acrylic acid tert-butyl ester (BIO117). To a solution of BIO114 (500 mg, 0.94 mmol) in aq. 50% THF (30 mL), LiOH·H2O (198 mg, 4.71 mmol) was added. The solution was stirred overnight at rt. The solvent was evaporated, the crude was diluted in 1N KHSO4 and extracted with EtOAc. The combined organic extracts were washed with brine, dried over anhydrous Na2SO4 and concentrated in vacuo, to give 462 mg (98%) of the title compound (white solid), m.p. 206° C. 1H-NMR (300 MHz, DMSO-d6): 7.76-7.60 (m, 4H), 7.56 (d, 1H, J=15.9 Hz), 7.47 (dd, 1H, J=2.0, 8.4 Hz), 7.43 (d, 1H, J=2.0 Hz), 6.80 (d, 1H, J=8.4 Hz), 6.51 (d, 1H, J=15.9 Hz), 4.91 (q, 1H, J=6.5 Hz), 2.24-2.00 (m, 9H), 1.79-1.66 (m, 6H), 1.57 (d, 3H, J=6.5 Hz), 1.47 (9H, s).

3-{3'-adamantan-1-yl-4'-[1-(tetrahydropyran-2-yloxycarbamoyl)-ethoxy]-biphenyl-4-yl}-acrylic acid tert-butyl ester (BIO118)

To a solution of BIO117 (400 mg, 0.79 mmol) in dry DMF (6 mL), HBTU (302 mg, 0.79 mmol) and DIPEA (423 µL, 2.38 mmol) were added at 0° C. under nitrogen atmosphere.

3-[3'-adamantan-1-yl-4'-(1-hydroxycarbamoy-lethoxy)-biphenyl-4-yl]-acrylic acid (GEM144)

To a solution of BIO118 (1.35 g, 2.20 mmol) in dry CH2Cl2 (22 mL) at 0° C., TFA (22 mL) was dropwise under nitrogen. The solution was stirred at 0° C. for 4h. The mixture was evaporated and treated with toluene to remove TFA, the solid obtained was triturated in CH2Cl2 and filtrated to give 646 mg of title compound. Yield: 64%. 1H-NMR (300 MHz, CDCl3+TFA): 7.92 (1H, d, J=15.9 Hz), 7.68-7.59 (4H, m), 7.57 (1H, d, J=2.2 Hz), 7.44 (1H, dd, J=2.2 Hz, 8.3 Hz), 6.80 (1H, d, J=8.3 Hz), 6.49 (1H, d, J=15.9 Hz), 5.10-4.95 (1H, m), 2.28-2.03 (9H, m), 1.91-1.68 (9H, m).

Synthesis of BIO146

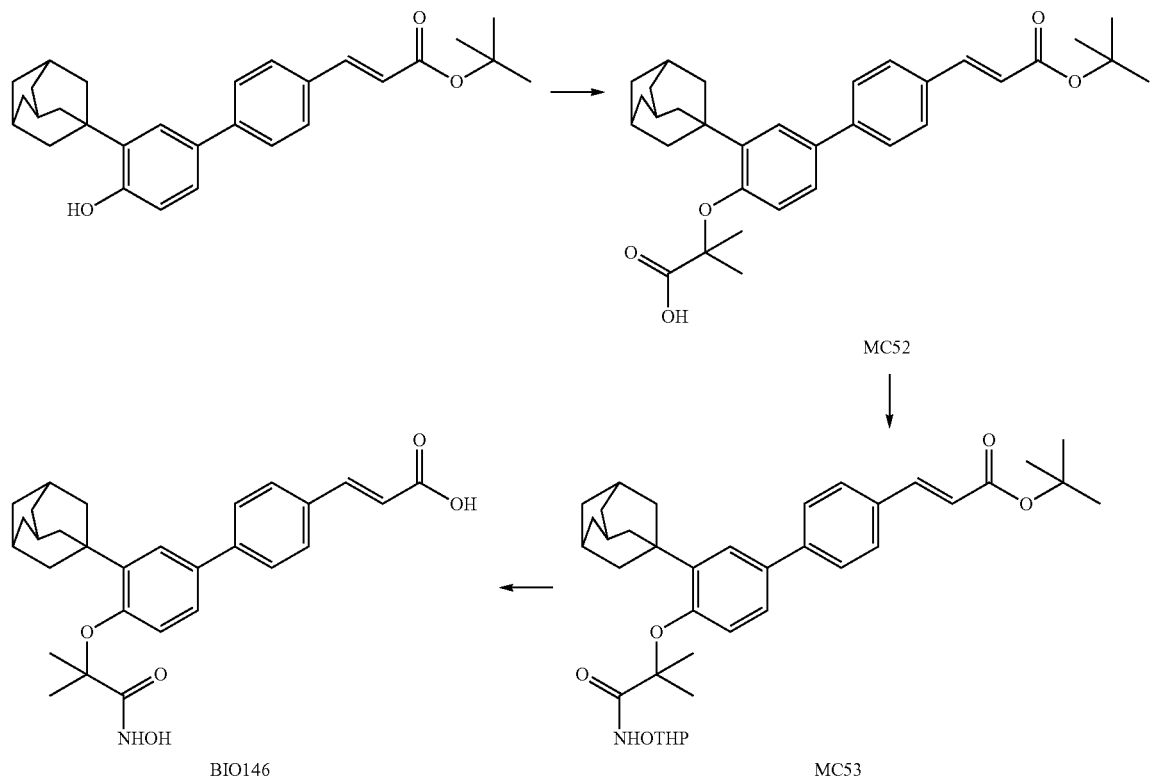

The solution was stirred 30 min at 0° C. then O-(tetrahydropyran-2-yl)-hydroxylamine (93 mg, 079 mmol) was added and the reaction was stirred overnight at rt. The solvent was removed in vacuo, the residue was triturated with water and filtered. The crude was purified by flash column chromatography in hexane:ethyl acetate 3:1 to give 400 mg of title compound. Yield: 84%. 1H-NMR (300 MHz, CDCl3): 8.98 (1H, s), 8.87 (1H, s), 7.61 (2H, d, J=15.8 Hz), 7.57-7.53 (8H, m), 7.51 (2H, d, J=2.3 Hz), 7.45-7.35 (2H, m), 6.91-6.83 (2H, m), 6.38 (2H, d, J=15.9 Hz), 5.03-4.81 (4H, m), 3.90-3.76 (2H, m), 3.64-3.54 (1H, m), 3.50-3.38 (1H, m), 2.26-2.07 (18H, m), 1.84-1.76 (12H, m), 1.69-1.74 (6H, m), 1.54 (18H, s).

3-[3'-adamantan-1-yl-4'-(1-carboxy-1-methyl-ethoxy)-biphenyl-4-yl]-acrylic acid tert-butyl ester (MC52)

To a solution of 3-(3'-adamantan-1-yl-4'-hydroxybiphenyl-4-yl)-acrylic acid tert-butyl ester (500 mg, 1.16 mmol) in methyl ethyl ketone (4.6 mL), NaOH (232 mg, 5.8 mmol, 5 equiv) was added under nitrogen atmosphere. The mixture was heated to 50° C. and a solution of α-bromoisobutyric acid (351 mg, 2.10 mmol, 1.8 equiv) in methyl ethyl ketone (1.3 mL) was added to the suspension. The reaction mixture was stirred 4 h at 50° C. The solvent was removed in vacuo, the crude was triturated with diethyl ether (50 mL) and the resulting solid was filtered. Then it was suspended in 1N KHSO4 and extracted with ethyl acetate (3×30 mL). The combined organic extracts were washed with brine, dried over anhydrous Na2SO4 and concentrated in vacuo to give 433 mg of the title compound (72% yield). 1H-NMR (300

MHz, DMSO-d6): δ 7.75-7.68 (2H, m), 7.65-7.59 (2H, m), 7.55 (1H, d, J=16 Hz), 7.46-7.41 (2H, m), 6.63 (1H, d, J=8.3 Hz), 6.51 (1H, d, J=16 Hz), 2.20-1.99 (9H, m), 1.80-1.65 (6H, m), 1.61 (6H, s), 1.47 (9H, s).

3-{3'-adamantan-1-yl-4'-[1-methyl-1-(tetrahydropyran-2-yloxycarbamoyl)-ethoxy]-biphenyl-4-yl}-acrylic acid tert-butyl ester (MC53)

To a solution of MC52 (300 mg, 0.55 mmol) in dry DMF (4.5 mL), HBTU (220 mg, 0.58 mmol) and DIPEA (300 µL, 1.74 mmol) were added at 0° C. under nitrogen atmosphere. The solution was stirred 30 min at 0° C. then O-(tetrahydropyran-2-yl)-hydroxylamine (68 mg, 058 mmol) was added and the reaction was stirred overnight at rt. The solvent was evaporated, the residue was poured into water and extracted with ethyl acetate. The organic phase was washed with water, brine, dried over anhydrous Na2SO4 and concentrated. The residue was purified by flash chromatography (petroleum ether:ethyl acetate 4:1) to give 150 mg (42%) of the title compound. 1H-NMR (300 MHz, CDCl3): δ 8.96 (1H, s), 7.60 (1H, d, J=15.7 Hz), 7.57-7.52 (4H, m), 7.50 81H, d, J=2.4 Hz), 7.34 (1H, dd, J=2.4 Hz, 8.6 Hz), 6.81 (1H, d, J=8.6 Hz), 6.38 (1H, d, J=15.7 Hz), 4.94-5.01 (1H, m), 3.97-3.86 (1H, m), 3.59-3.50 (1H, m) 2.21-2.06 (9H, m), 1.87-1.76 (10H, m), 1.73 (3H, s), −1.69 (3H, s), 1.59-1.55 (2HH, m), 1.54 (9H, s).

3-[3'-adamantan-1-yl-4'-(1-hydroxycarbamoyl-1-methylethoxy)-biphenyl-4-yl]-acrylic acid (BIO146)

To a solution of MC53 (132 mg, 0.21 mmol) in dry CH2Cl2 (2.1 mL) at 0° C., TFA (2.1 mL) was added dropwise under nitrogen. The solution was stirred at 0° C. for 5 h. The mixture was evaporated and treated with toluene to remove TFA, the solid obtained was triturated in CH2Cl2 and filtrated to give 69 mg of the title compound. Yield: 69%. 1H-NMR (300 MHz, CDCl3+TFA) δ: 7.91 (1H, d, J=15.8 Hz), 7.67-7.58 (4H, m), 7.56 (1H, d, J=2.1 Hz), 7.38 (1H, dd, J=2.1 Hz, 8.4 Hz), 6.66 (1H, d, J=8.4 Hz), 6.49 (1H, d, J=15.8 Hz), 2.21-2.08 (9H, m), 1.88-1.69 (12H, m).

Evaluation of Cytotoxicity

The anti-proliferative activity of GEM144 and BIO146 was assessed in vitro on a number of cell lines from solid and hematological human cancers.

To this end, cells in the logarithmic phase of growth were seeded in 96-wells plastic plates, incubated overnight in culture medium, and treated for 72 h with scalar concentrations (2-fold dilution series) of the compounds. Cell survival was finally assayed by the SRB (solid tumors) or MTT (blood tumors) test and the IC50 value (drug concentration inhibiting 50% of cell growth) calculated by the ALLFIT program.

BIO146 and GEM144 were previously tested on NCI-H460 NSCLC cells.

According to the SRB/MTT assay, BIO146 showed on NCI-H460 cells a cytotoxic activity in the micro molar range, while GEM144 was highly effective with an IC50 value in the nano molar range (Table 1). As a consequence, GEM144 underwent further evaluations on a broader number of tumor cell lines. The compound displayed a high cytotoxic potency (IC50<1 µM) on parental A2780 and multidrug-resistant A2780-Dx ovarian carcinoma cells, resulting at the same time a very poor substrate for the P-gp drug efflux pump, as indicated by low resistance index value (RI<1). Moreover, GEM144 resulted very effective as tested against other solid (MM473 and MM487 mesothelioma, DU145 prostate carcinoma, HT29 and SW620 colon carcinomas, B16 melanoma) and hematological (THP-1 leukemia, U2932 and Z138 lymphoma) tumor cell lines, as well (Tables 1-2).

Table 12 is illustrated in FIG. 2; Solid cancer cell lines exposed to GEM144 and BIO146. Tumor cells were exposed to the inhibitors, and the anti-proliferative activity assessed upon 72 h with the SRB assay. N.e.=not evaluated.

Table 13 is illustrated in FIG. 3: Human hematological tumor cell lines exposed to GEM144 and BIO146. Tumor cells were treated with inhibitors and cell survival assessed upon 72 h with the MTT assay. N.e.=not evaluated.

Cell Lines

Human NCI-H460 and H460-R9A (atypical retinoid-resistant NCI-H460) NSCLC; A2780 and A2780-Dx (multidrug resistant) ovarian carcinoma; MM473-Luc, and MM487-Luc mesothelioma; HT29 and SW620 colon carcinoma; DU145 prostate carcinoma; Z-138 mantle cell lymphoma and U-2932 diffuse large B-cell lymphoma; NB4 pro-myelocitic leukemia and THP-1 monocytic leukemia; mouse B16-Luc melanoma.

Cell Cultures

NCI-H460, H460-R9A, A2780, A2780-Dx, NB4, B16-Luc cells were cultured in RPMI-1640 medium supplemented with 10% FBS, 2 mM L-glutamine and gentamicin sulphate. Z-138, U-2932, THP-1, DU145, SW620 cells were cultured in DMEM medium supplemented with 10% FBS, 2 mM L-glutamine and gentamicin sulphate. MM473-Luc, and MM487-Luc cells were cultured in Ham's F-10 Nutrient Mixture supplemented with 10% FBS, 2 mM L-glutamine, 0.05 mg/mL gentamicin sulphate, and 0.4 mg/mL G418 antibiotic. HT29 cells were cultured in McCoy's medium supplemented with 10% FBS, 2 mM L-glutamine and 0.05 mg/mL gentamicin sulphate.

Cells were maintained in a 37° C. incubator with saturated humidity and an atmosphere of 95% air and 5% CO2, and were sub-cultured every 2-3 days.

A number of embodiments of the invention have been described. Nevertheless, it can be understood that various modifications may be made without departing from the spirit and scope of the invention. Accordingly, other embodiments are within the scope of the following claims.

What is claimed is:

1. A method for treating an altered angiogenesis comprising administration to an individual in need thereof a medicament or pharmaceutical composition comprising:
   (a) 3-(3'-adamantan-1-yl-4'-hydroxycarbamoylmethoxy biphenyl-4-yl)-acrylic acid (MIR002);
   (b) 3-[3'-adamantan-1-yl-4'-(1-hydroxycarbamoylethoxy)-biphenyl-4-yl]-acrylic acid (GEM144); or
   (c) a combination of (a) and (b).

2. A method for treating a disease selected from the group consisting of an arthritic pathology, a tumor, a metastatization, diabetic retinopathy, psoriasis and chronic inflammatory disease,
   the method comprising administration to an individual in need thereof a medicament or pharmaceutical composition comprising:
   (a) 3-(3'-adamantan-1-yl-4'-hydroxycarbamoylmethoxybiphenyl-4-yl)-acrylic acid (MIR002);
   (b) 3-[3'-adamantan-1-yl-4'-(1-hydroxycarbamoylethoxy)-biphenyl-4-yl]-acrylic acid (GEM144); or
   (c) a combination of (a) and (b).

3. The method of claim 2, wherein said tumour is selected from the group consisting of sarcoma, carcinoma, carcinoid, mesothelioma, lymphoma, bone tumour, neuroendocrine tumour, lymphoid leukaemia, myeloid leukaemia, monocytic leukaemia, megakaryocytic leukaemia, acute promyelocytic leukaemia, Hodgkin's disease, lung tumour, hepatoma, mesothelioma, intracranial tumor and glioma.

4. The method of claim 1, wherein the medicament or pharmaceutical composition is formulated for oral administration and is orally administered.

5. The method of claim 2, wherein the medicament or pharmaceutical composition is formulated for oral administration and is orally administered.

6. The method of claim 1, wherein the medicament or pharmaceutical composition further comprises or is contained within a pharmaceutically acceptable vehicle or excipient.

7. The method of claim 2, wherein the medicament or pharmaceutical composition further comprises or is contained within a pharmaceutically acceptable vehicle or excipient.

8. The method of claim 1, wherein the medicament or pharmaceutical composition further comprises: a formulation co-adjuvant; or, a solubilizing agent, a dispersing agent, a suspension agent or an emulsifying agent.

9. The method of claim 2, wherein the medicament or pharmaceutical composition further comprises: a formulation co-adjuvant; or, a solubilizing agent, a dispersing agent, a suspension agent or an emulsifying agent.

10. The method of claim 1, wherein the medicament or pharmaceutical composition further comprises one or more chemotherapeutic agents.

11. The method of claim 10, wherein the chemotherapeutic agent comprises a platinum-based chemotherapeutic agent.

12. The method of claim 2, wherein the medicament or pharmaceutical composition further comprises one or more chemotherapeutic agents.

13. The method of claim 12, wherein the chemotherapeutic agent comprises a platinum-based chemotherapeutic agent.

14. The method of claim 4, wherein the medicament or pharmaceutical composition is orally administered at a dosage of between about 0.01 mg/kg to 100 mg/kg.

15. The method of claim 5, wherein the medicament or pharmaceutical composition is orally administered at a dosage of between about 0.01 mg/kg to 100 mg/kg.

16. The method of claim 1, wherein the altered angiogenesis is caused by a chronic inflammatory disease.

17. The method of claim 2, wherein the disease is arthritic pathology.

18. The method of claim 2, wherein the disease is diabetic retinopathy.

19. The method of claim 2, wherein the disease is psoriasis.

20. The method of claim 2, wherein the disease is chronic inflammatory disease.

* * * * *